United States Patent
Seo et al.

(10) Patent No.: US 7,879,317 B2
(45) Date of Patent: Feb. 1, 2011

(54) POLYMERIC MICELLE COMPOSITIONS WITH IMPROVED STABILITY AND METHODS OF MAKING THEREOF

(75) Inventors: Min-Hyo Seo, Daejeon (KR); Sa-Won Lee, Daejeon (KR); Hee-Jo Kim, Daejeon (KR); Jeong-Kyung Kim, Daejeon (KR); Myung-Han Huyn, Daejeon (KR); Jeong-il Yu, Daejeon (KR); Bong-Oh Kim, Daejeon (KR)

(73) Assignee: Samyang Corporation, Seoul (KR)

( * ) Notice: Subject to any disclaimer, the term of this patent is extended or adjusted under 35 U.S.C. 154(b) by 1287 days.

(21) Appl. No.: 10/493,043

(22) PCT Filed: Oct. 17, 2002

(86) PCT No.: PCT/KR02/01942

§ 371 (c)(1), (2), (4) Date: Apr. 15, 2004

(87) PCT Pub. No.: WO03/033592

PCT Pub. Date: Apr. 24, 2003

(65) Prior Publication Data

US 2004/0253195 A1 Dec. 16, 2004

(30) Foreign Application Priority Data

Oct. 18, 2001 (KR) ............... 2001-64468
Dec. 4, 2001 (KR) ............... 2001-76213

(51) Int. Cl.
*A61K 8/72* (2006.01)
*A61K 31/74* (2006.01)
(52) U.S. Cl. ............... 424/70.11; 424/78.27; 424/78.08
(58) Field of Classification Search ............. 424/70.11, 424/78.27, 78.08
See application file for complete search history.

(56) References Cited

U.S. PATENT DOCUMENTS

| 5,429,826 A | 7/1995 | Nair et al. |
| 5,449,513 A | 9/1995 | Yokoyama et al. |

(Continued)

FOREIGN PATENT DOCUMENTS

AU    2001-262756 B2    11/2001

(Continued)

OTHER PUBLICATIONS

Kim et al., ("Core-stabilized Polymeric Micelle as Potential Drug Carrier: Increased Solubilization of Taxol," in Polym. Adv. Techno. 10, 647-654 (1999)).*

(Continued)

*Primary Examiner*—Blessing M Fubara
(74) *Attorney, Agent, or Firm*—Birch, Stewart, Kolasch & Birch, LLP

(57) ABSTRACT

Polymeric compositions capable of forming stable micelles in an aqueous solution, comprising an amphiphilic block copolymer of a hydrophilic block and a hydrophobic block, and a polylactic acid derivative wherein one end of the polylactic acid is covalently bound to at least one carboxyl group. The carboxyl group of the polylactic acid derivative may be fixed with a di- or tri-valent metal ion, obtained by adding the di- or tri-valent metal ion to the polymeric composition.

73 Claims, 5 Drawing Sheets

U.S. PATENT DOCUMENTS

| | | | |
|---|---|---|---|
| 5,578,325 A * | 11/1996 | Domb et al. | 424/501 |
| 6,267,987 B1 | 7/2001 | Park et al. | |
| 6,447,796 B1 * | 9/2002 | Vook et al. | 424/422 |
| 6,743,446 B2 * | 6/2004 | Schwendeman et al. | 424/486 |
| 6,916,788 B2 * | 7/2005 | Seo et al. | 514/12 |
| 7,153,520 B2 * | 12/2006 | Seo et al. | 424/426 |

FOREIGN PATENT DOCUMENTS

| | | |
|---|---|---|
| EP | 0 552 802 A2 | 7/1993 |
| EP | 0 583 955 A2 | 2/1994 |
| JP | 3-45265 A | 2/1991 |
| JP | 5-279468 A | 10/1993 |
| JP | 206815 | 7/1994 |
| JP | 7-69917 A | 3/1995 |
| JP | 10-110019 A | 4/1998 |
| WO | WO 9503357 * | 2/1995 |
| WO | WO99/29758 | 6/1999 |
| WO | WO01/12718 | 2/2001 |
| WO | WO-01/87345 A1 | 11/2001 |

OTHER PUBLICATIONS

Zhang et al. ("Effects of metal salts on poly (DL-lactide-co-glycolide) polymer hydrolysis," in Journal of Biomedical Materials Research, vol. 34, 531-538 (1997).*

* cited by examiner

POLYMERIC MICELLE COMPOSITIONS WITH IMPROVED STABILITY AND METHODS OF MAKING THEREOF

This application claims benefit of a patent application filed earlier as PCT International Application No. PCT/KR02/01942, filed on Oct. 17, 2002, which claims priority to Korean Application No. 2001/76213, filed on Dec. 4, 2001, and Korean Application No. 2001/64468, filed on Oct. 18, 2001.

BACKGROUND OF THE INVENTION

1. Field of the Invention

The present invention relates to a polymeric micelle composition, and more specifically, to a polymeric micelle composition comprising an amphiphilic block copolymer composed of a hydrophilic block and a hydrophobic block, and a polylactic acid derivative having at least one terminal carboxyl group.

2. Related Art

Recently, nanoparticle and polymeric micelle systems using biodegradable polymers have been reported to be extremely useful technologies which can alter the in vivo distribution of an intravenously administered drug thereby reducing its side effects and improving its efficacy. These systems offer advantages such as specific cell targeting and control of the release of the drug. They also have good compatibility with body fluids and improve the solubility and bioavailability of poorly water-soluble drugs.

A method for preparing block copolymer micelles by physically entrapping a drug in the block copolymer which is composed of a hydrophilic component and a hydrophobic component was disclosed in EP 0 583,955A2, and JP 206, 815/94. The block copolymer employed is an A-B type diblock copolymer comprising a polyethylene oxide as the hydrophilic A component and a polyamino acid or derivatives thereof having a hydrophobic functional group as the hydrophobic B component. Polymeric micelles comprising the above block copolymer can physically incorporate a drug, e.g. adriamycin, indomethacin, etc. into the inner core of the polymeric micelles, which can then be used as a drug delivery carrier. However, these polymeric micelles are comprised of block copolymers that cannot be readily degraded in vivo. In addition, the b lock copolymers have poor biocompatibility, which can cause undesirable side effects when administered in vivo.

Great effort has been devoted to the development of a biodegradable and biocompatible core-shell type drug carrier with improved stability and efficacy, and which will entrap a poorly water-soluble drug. A method for preparation of chemically fixed polymeric micelles, wherein the polymer is a core-shell type polymer comprising a hydrophilic polyethylene oxide as the shell and a hydrophobic biodegradable polymer that is cross-linked in an aqueous solution as the core, was disclosed in EP 0,552,802A2. However, this polymeric micelle is difficult to prepare because crosslinkers must be introduced into the hydrophobic component of the A-B type diblock or A-B-A type triblock copolymer so that the core-forming polymer has a stable structure. Also, administering a crosslinker that has never been used in the human body leads to safety concerns.

On the other hand, in order to solubilize a hydrophobic drug, there has been reported a polymeric micelle composed of a di- or tri-block copolymer comprising a hydrophilic polymer of polyalkylene glycol derivatives and a hydrophobic biodegradable polymer such as fatty acid polyesters or polyamino acids. U.S. Pat. No. 5,449,513 discloses a diblock copolymer comprising polyethylene glycol as the hydrophilic polymer, and a polyamino acid derivative, e.g. polybenzyl aspartic acid, etc. as the hydrophobic polymer. This diblock copolymer can solubilize hydrophobic anticancer agents, e.g. doxorubicin, or anti-inflammatory agents, e.g. indomethacin. However, the polyamino acid derivatives cannot be hydrolyzed in vivo, and thus cause side effects due to immune responses.

U.S. Pat. No. 5,429,826 discloses a di- or multi-block copolymer comprising a hydrophilic polyalkylene glycol and a hydrophobic polylactic acid. Specifically, the above patent describes a method of stabilizing polymeric micelles by micellizing a di- or multi-block copolymer wherein an acrylic acid derivative is bonded to a terminal group of the di- or multi-block copolymer in an aqueous solution, which then crosslinks the polymers in order to form the micelles. The above method could accomplish stabilization of the polymeric micelle, but the crosslinked polymer is not degraded, and thus, cannot be applied for in vivo use. The above polymeric micelles can solubilize a large amount of a poorly water-soluble drug in an aqueous solution with a neutral pH, but have the drawback that they release the drug within a short period of time.

In view of the foregoing, development of an improved polymeric micelle composition for hydrophobic drug delivery that is biocompatible and biodegradable will be appreciated and desired. Thus, the present invention provides such an improved polymeric micelle composition which is biocompatible and biodegradable and which can effectively deliver a hydrophobic drug without a decrease in its stability.

SUMMARY OF THE INVENTION

The present invention relates to a polymeric micelle composition comprising an amphiphilic block copolymer and a polylactic acid derivative containing at least one carboxyl terminal group. The present invention also relates to a polymeric composition wherein the carboxyl terminal group of the polylactic acid derivative is fixed with a di- or tri-valent metal ion. The compositions of the present invention can form stable polymeric micelles or nanoparticles in body fluids or aqueous solutions. The micelles or nanoparticles formed from the compositions of the present invention have a hydrophilic outer shell and a hydrophobic inner core wherein a large amount of hydrophobic drug can be physically trapped. The drug containing micelles and nanoparticles of the present invention have a prolonged retention time in the bloodstream after administration, and can be utilized to make various pharmaceutical formulations. Additional features and advantages of the invention will be apparent from the detailed description that follows, which when taken in conjunction with the accompanying drawings together illustrate, by way of example, features of the invention.

DETAILED DESCRIPTION OF THE INVENTION

Figure 1:
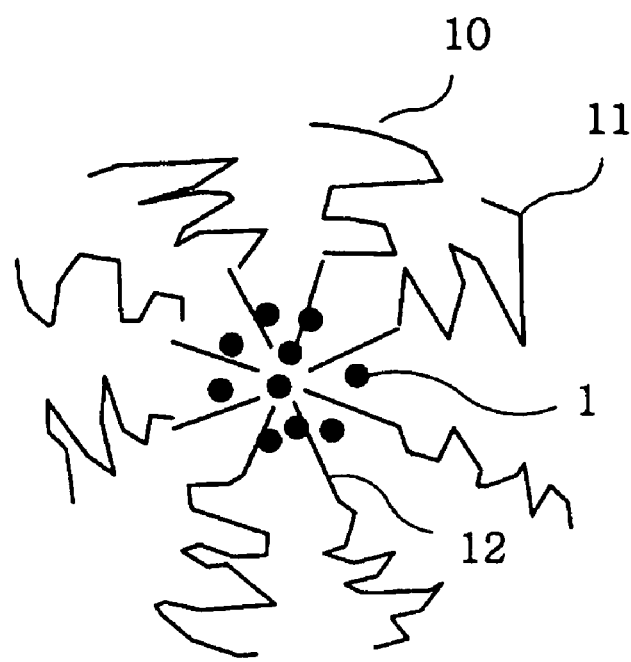
FIG. 1 is a schematic diagram of a polymeric micelle formed by monomethoxypolyethylene glycol-polylactide (mPEG-PLA) in an aqueous environment.

Before the present polymeric compositions and methods of using and making thereof are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise. Thus, for example, reference to a polymer containing "a terminal group" includes reference to two or more such groups, and reference to "a hydrophobic drug" includes reference to two or more of such drugs.

In describing and claiming the present invention, the following terminology will be used in accordance with the definitions set out below.

As used herein, the term "bioactive agent" or "drug" or any other similar term means any chemical or biological material or compound suitable for administration by methods previously known in the art and/or by the methods taught in the present invention and that induce a desired biological or pharmacological effect. Such effects may include but are not limited to (1) having a prophylactic effect on the organism and preventing an undesired biological effect such as preventing an infection, (2) alleviating a condition caused by a disease, for example, alleviating pain or inflammation caused as a result of disease, and/or (3) either alleviating, reducing, or completely eliminating a disease from the organism. The effect may be local, such as providing for a local anesthetic effect, or it may be systemic.

As used herein, the term "biodegradable" or "biodegradation" is defined as the conversion of materials into less complex intermediates or end products by solubilization hydrolysis, or by the action of biologically formed entities which can be enzymes or other products of the organism.

As used herein, the term "biocompatible" means materials or the intermediates or end products of materials formed by solubilization hydrolysis, or by the action of biologically formed entities which can be enzymes or other products of the organism and which cause no adverse effects on the body.

"Poly(lactide)" or "PLA" shall mean a polymer derived from the condensation of lactic acid or by the ring opening polymerization of lactide. The terms "lactide" and "lactate" are used interchangeably.

As used herein, "effective amount" means the amount of a bioactive agent that is sufficient to provide the desired local or systemic effect and performance at a reasonable risk/benefit ratio as would attend any medical treatment.

As used herein, "administering" and similar terms means delivering the composition to the individual being treated such that the composition is capable of being circulated systemically. Preferably, the compositions of the present invention are administered by the subcutaneous, intramuscular, transdermal, oral, transmucosal, intravenous, or intraperitoneal routes. Injectables for such use can be prepared in conventional forms, either as a liquid solution or suspension, or in a solid form that is suitable for preparation as a solution or suspension in a liquid prior to injection, or as an emulsion. Suitable excipients that can be used for administration include, for example, water, saline, dextrose, glycerol, ethanol, and the like; and if desired, minor amounts of auxiliary substances such as wetting or emulsifying agents, buffers, and the like can be used. For oral administration, it can be formulated into various forms such as solutions, tablets, capsules, etc.

Reference will now be made to the exemplary embodiments and specific language will be used herein to describe the same. It will nevertheless be understood that no limitation of the scope of the invention is thereby intended. Alterations and further modifications of the inventive features illustrated herein, and additional applications of the principles of the invention as illustrated herein, which would occur to one skilled in the relevant art and having possession of this disclosure, are to be considered within the scope of the invention.

One aspect of the present invention is a polymeric composition capable of entrapping a large amount of a hydrophobic drug and forming stable polymeric micelles or nanoparticles in an aqueous environment. Specifically, the present invention provides a polymeric composition comprising an amphiphilic block copolymer composed of a hydrophilic block and hydrophobic block, and a polylactic acid derivative having a carboxyl terminal group, wherein said composition forms stable polymeric micelles in an aqueous environment.

Another aspect of the present invention provides a polymeric composition comprising an amphiphilic block copolymer comprised of a hydrophilic block and a hydrophobic block, and a polylactic acid derivative having a carboxyl terminal group that is bound with a di- or tri-valent metal ion.

The present invention also provides a pharmaceutical composition comprising polymeric micelles or nanoparticles formed by the above polymeric composition having a hydrophobic drug entrapped therein. The present invention further provides a process for preparing the above pharmaceutical composition.

The amphiphilic block copolymer of the present invention is preferably an A-B type diblock copolymer comprising a hydrophilic A block and a hydrophobic B block. The amphiphilic block copolymer, when placed in an aqueous phase, forms core-shell type polymeric micelles wherein the hydrophobic B block forms the core and the hydrophilic A block forms the shell. Preferably, the hydrophilic A block is a member selected from the group consisting of polyalkylene glycol, polyvinyl alcohol, polyvinyl pyrrolidone, is polyacryl amide and derivatives thereof. More preferably, the hydrophilic A block is a member selected from the group consisting of monomethoxypolyethylene glycol, monoacetoxypolyethylene glycol, polyethylene glycol, polyethylene-co-propylene glycol, and polyvinyl pyrrolidone. Preferably, the hydrophilic A block has a number average molecular weight of 500 to 50,000 Daltons. More preferably, the hydrophilic A block has a number average molecular weight of 1,000 to 20,000 Daltons.

The hydrophobic B block of the amphiphilic block copolymer of the present invention is a highly biocompatible and biodegradable polymer selected from the group consisting of polyesters, polyanhydrides, polyamino acids, polyorthoesters and polyphosphazine. More preferably, the hydrophobic B block is a member selected from the group consisting of polylactides, polyglycolides, polycaprolactone, polydioxan-2-one, polylactic-co-glycolide, polylactic-co-dioxan-2-one, polylactic-co-caprolactone, and polyglycolic-co-caprolactone. The hydroxyl terminal group of the hydrophobic B block can be substituted with a fatty acid such as butyric acid, propionic acid, acetic acid, stearic acid or palmitic acid. Preferably, the hydrophobic B block of the amphiphilic block copolymer has a number average molecular weight of 500 to 50,000 Daltons. More preferably, the hydrophobic B block of the amphiphilic block copolymer has a number average molecular weight 1,000 to 20,000 Daltons.

The ratio of the hydrophilic A block to the hydrophobic B block of the amphiphilic block copolymer of the present invention is preferably within the range of 2:8 to 8:2, and more preferably within the range of 4:6 to 7:3. If the content of the hydrophilic A block is too low, the polymer may not form polymeric micelles in an aqueous solution, and if the content is too high, the polymeric micelles formed are not stable.

At least one terminal end of the polylactic acid derivative of the present invention is covalently bound to at least one carboxylic acid or carboxylate salt. The other terminal end of the polylactic acid derivative of the present invention may be covalently bound to a functional group selected from the group consisting of hydroxyl, acetoxy, benzoyloxy, decanoyloxy and palmitoyloxy groups. The carboxylic acid or carboxylate salt functions as a hydrophilic group in an aqueous solution of pH 4 or more and enables the polylactic acid derivative to form polymeric micelles therein. When the polylactic acid derivatives of the present invention are dissolved in an aqueous solution, the hydrophilic and hydrophobic components present in the polylactic acid derivative should be balanced in order to form polymeric micelles. Therefore, the number average molecular weight of the polylactic acid derivative of the present invention is preferably within the range of 500 to 2,500 Daltons. The molecular weight of the polylactic acid derivative can be adjusted by controlling the reaction temperature, time, and the like, during the preparation process.

The polylactic acid derivative is preferably represented by the following formula:

RO—CHZ-[A]$_n$-[B]$_m$—COOM (I)

wherein A is —COO—CHZ—; B is —COO—CHY—, —COO—CH$_2$CH$_2$CH$_2$CH$_2$CH$_2$— or —COO—CH$_2$CH$_2$OCH$_2$; R is a hydrogen atom, acetyl, benzoyl, decanoyl, palmitoyl, methyl or ethyl group; Z and Y each are a hydrogen atom, methyl, or phenyl group; M is H, Na, K, or Li; n is an integer from 1 to 30, and m is an integer from 0 to 20.

One end of the polylactic acid derivative of the present invention is covalently bound to a carboxyl group or an alkali metal salt thereof, preferably, an alkali metal salt thereof. The metal ion in the alkali metal salt which forms the polylactic acid derivative is monovalent, e.g. sodium, potassium or lithium. The polylactic acid derivative in the metal ion salt form is a solid at room temperature, and is very stable because of its relatively neutral pH.

More preferably, the polylactic acid derivative is represented by the following formula:

RO—CHZ—[COO—CHX]$_p$—[COO—CHY']$_q$—COO—CHZ—COOM (II)

wherein X is a methyl group; Y' is a hydrogen atom or phenyl group; p is an integer from 0 to 25; q is an integer from 0 to 25, provided that p+q is an integer from 5 to 25; R, Z and M are the same as defined in Formula (I).

In addition, polylactic acid derivatives of the following formulas (III) and (IV) are also suitable for the present invention:

RO—PLA-COO—W-M' (III)

wherein W-M' is

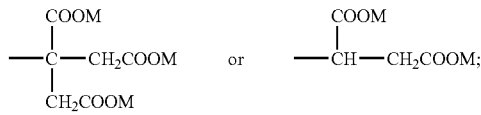

the PLA is a member selected from the group consisting of D,L-polylactic acid, D-polylactic acid, polymandelic acid, a copolymer of D,L-lactic acid and glycolic acid, a copolymer of D,L-lactic acid and mandelic acid, a copolymer of D,L-lactic acid and caprolactone, and a copolymer of D,L-lactic acid and 1,4-dioxan-2-one; R and M are the same as defined in Formula (I).

S—O—PLA-COO-Q (IV)

wherein S is

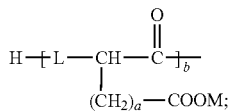

L is —NR$_1$— or —O—; R$_1$ is a hydrogen atom or C$_{1-10}$alkyl; Q is CH$_3$, CH$_2$CH$_3$, CH$_2$CH$_2$CH$_3$, CH$_2$CH$_2$CH$_2$CH$_3$, or CH$_2$C$_6$H$_5$; a is an integer from 0 to 4; b is an integer from 1 to 10; R and M are the same as defined in Formula (I); and PLA is the same as defined in Formula (III).

The polymeric composition of the present invention may contain 5 to 95 wt % of the amphiphilic block copolymer and 5 to 95 wt % of the polylactic acid derivative based on the total weight of the composition. Preferably, the polymeric composition of the present invention contains 20 to 80 wt % of the amphiphilic block copolymer and 20 to 80 wt % of the polylactic acid derivative. More preferably, the polymeric composition of the present invention contains 50 to 80 wt % of the amphiphilic block copolymer and 20 to 50 wt % of the polylactic acid derivative.

The polylactic acid derivatives of the present invention alone can form micelles in an aqueous solution of pH 4 or more; however, the polymeric compositions can form micelles in an aqueous solution irrespective of the pH of the solution. Since the biodegradable polymer is usually hydrolyzed at a pH of 10 or more, the polymeric compositions of the present invention may be used at a pH within the range of 1 to 10, preferably at a pH within the range of 4 to 8. The particle size of the micelles or nanoparticles prepared from the polymeric compositions of the present invention may be adjusted to be within the range of 1 to 400 nm, and preferably from 5 to 200 nm, depending on the molecular weight of the polymers and the ratio of the polylactic acid derivative to the amphiphilic block copolymer.

Figure 2:
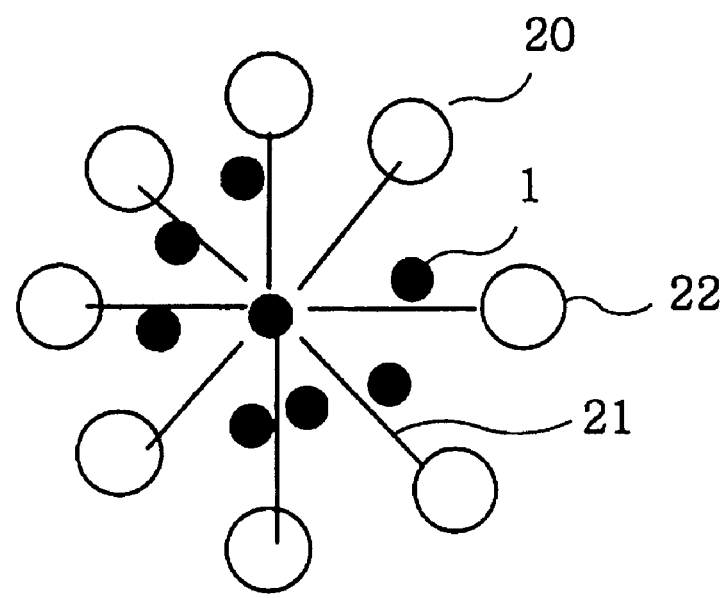
FIG. 2 is a schematic diagram of a polymeric micelle formed by sodium carboxylate derivatized D,L-polylactic acid in an aqueous environment.
Figure 3:
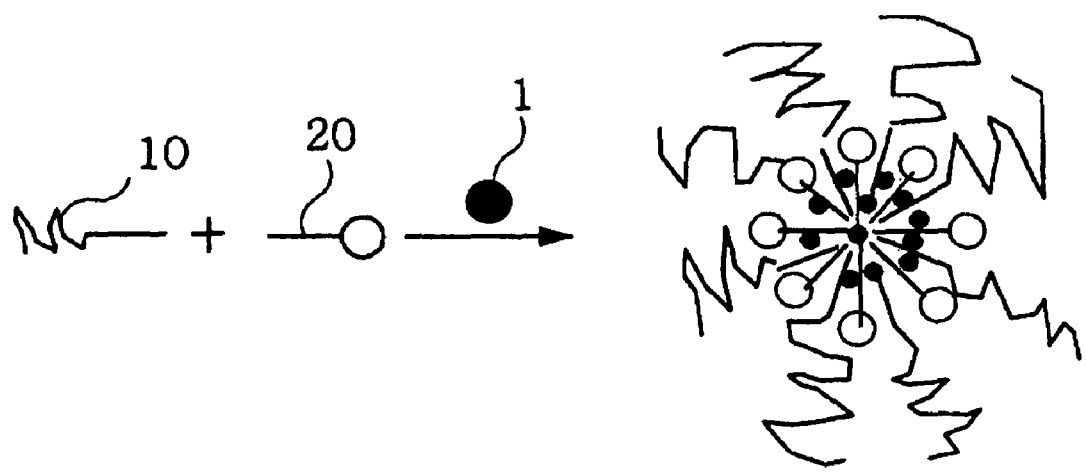
FIG. 3 is a schematic diagram of a polymeric micelle formed by a mixture of monomethoxypolyethylene glycol-polylactide (mPEG-PLA) and sodium carboxylate derivatized D,L-polylactic acid in an aqueous environment.

As illustrated in FIG. 1 to FIG. 3, the polylactic acid derivatives or the amphiphilic block copolymers alone and mixtures thereof may form micelles in an aqueous solution. 1 represents poorly water-soluble drugs; 10 represents monomethoxypolyethylene glycol-polylactide (mPEG-PLA); 11 represents monomethoxypolyethylene glycol (mPEG); 12 represents polylactide (PLA); 20 represents the sodium salt of D,L-poly(lactic acid); 21 represents D,L-polylactic acid; and 22 represents sodium carboxylate. However, the polymeric compositions of the present invention remarkably improve the drug loading efficiency and stability of the micelles formed in an aqueous solution compared with the micelles formed from the polylactic acid derivatives or the amphiphilic block copolymers alone.

According to the following examples, the polymeric micelles composed of the polylactic acid derivative alone may contain up to 25 wt % of paclitaxel, but the paclitaxel is released within 1 hour at 37° C. in an aqueous solution. In addition, the polymeric micelles composed of the amphiphilic block copolymer alone may contain 5 wt % or less of paclitaxel, and the paclitaxel is released in 6 hours at 37° C. in an aqueous solution. In contrast, the polymeric micelles composed of the composition of the present invention comprising an amphiphilic block copolymer and a polylactic acid derivative may contain up to 25 wt % of paclitaxel, and less than at most 1.0% (w/w)of the paclitaxel is released within 24 hours at 37° C. in an aqueous solution.

The loading efficiency of a drug into the polymeric micelles is in proportion to the fraction of the hydrophobic block that forms the hydrophobic core of the micelle that is formed in an aqueous solution. The stability of the polymeric micelles in an aqueous solution depends on their dynamic equilibrium in the aqueous solution, i.e. the equilibrium constant between the states of the polymeric micelle and a single polymer dissolved in water. The polylactic acid derivative is very hydrophobic because the hydrophilic component, namely the carboxylic acid terminal group, comprises 10% or less of the polymer. Therefore, the polymeric micelles formed by polylactic acid derivatives alone may contain a large amount of a hydrophobic drug therein, but the micelles formed are very unstable due to electrostatic repulsion between the carboxyl anionic groups present in the terminus of the polymeric micelles. On the other hand, it is difficult for micelles formed from an amphiphilic block copolymer of monomethoxypolyethylene glycol (MN: 5,000 Daltons) and polylactide (MN: 4,000 Daltons) to contain a large amount of a hydrophobic drug because the hydrophobic block comprises only about 40% of the polymer. However, the micelles are very stable because the terminal hydrophilic groups of the amphiphilic block copolymer are non-ionic polyethylene glycol, which exhibit no electrostatic repulsion in contrast to the polylactic acid derivatives. Therefore, by combining amphiphilic block copolymers and polylactic acid derivatives, the present invention provides a polymeric micelle composition which can solubilize a large amount of a poorly water-soluble drug, and maintain stability for 24 hours or more.

In one embodiment of the present invention, the carboxyl terminal group of the polylactic acid derivative is bound or fixed with a di- or tri-valent metal ion. The metal ion-fixed polymeric composition can be prepared by adding the di- or tri-valent metal ion to the polymeric composition of the amphiphilic block copolymer and the polylactic acid derivative. The polymeric micelles or nanoparticles may be formed by changing the amount of the di- or tri-valent metal ion added for binding or fixing the carboxyl terminal group of the polylactic acid derivative.

The di- or tri-valent metal ion is preferably a member selected from the group consisting of $Ca^{2+}$, $Mg^{2+}$, $Ba^{2+}$, $Cr^{2+}$, $Fe^{2+}$, $Mn^{2+}$, $Ni^{2+}$, $Cu^{2+}$, $Zn^{2+}$, and $Al^{3+}$. The di- or tri-valent metal ion may be added to the polymeric composition of the amphiphilic block copolymer and the polylactic acid derivative in the form of a sulfate, chloride, carbonate, phosphate or hydroxylate, and preferably, in the form of $CaCl_2$, $MgCl_2$, $ZnCl_2$, $AlCl_3$, $FeCl_3$, $CaCO_3$, $MgCO_3$, $Ca_3(PO_4)_2$, $Mg_3(PO_4)_2$, $AlPO_4$, $MgSO_4$, $Ca(OH)_2$, $Mg(OH)_2$, $Al(OH)_3$, or $Zn(OH)_2$.

Figure 4:
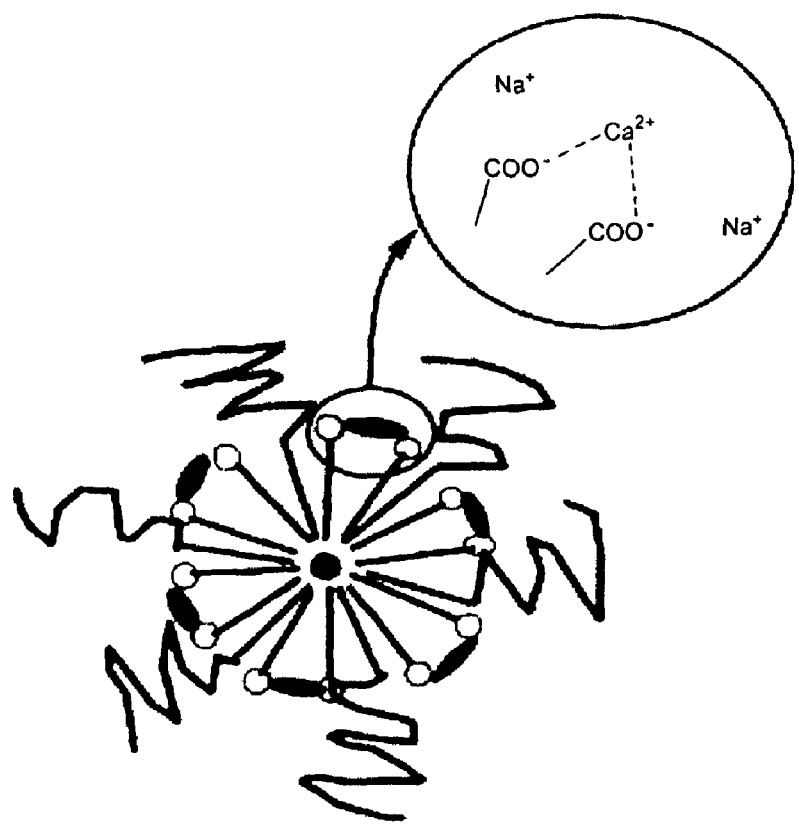
FIG. 4 is a schematic diagram of a $Ca^{2+}$-fixed polymeric micelle of FIG. 3.
Figure 5:
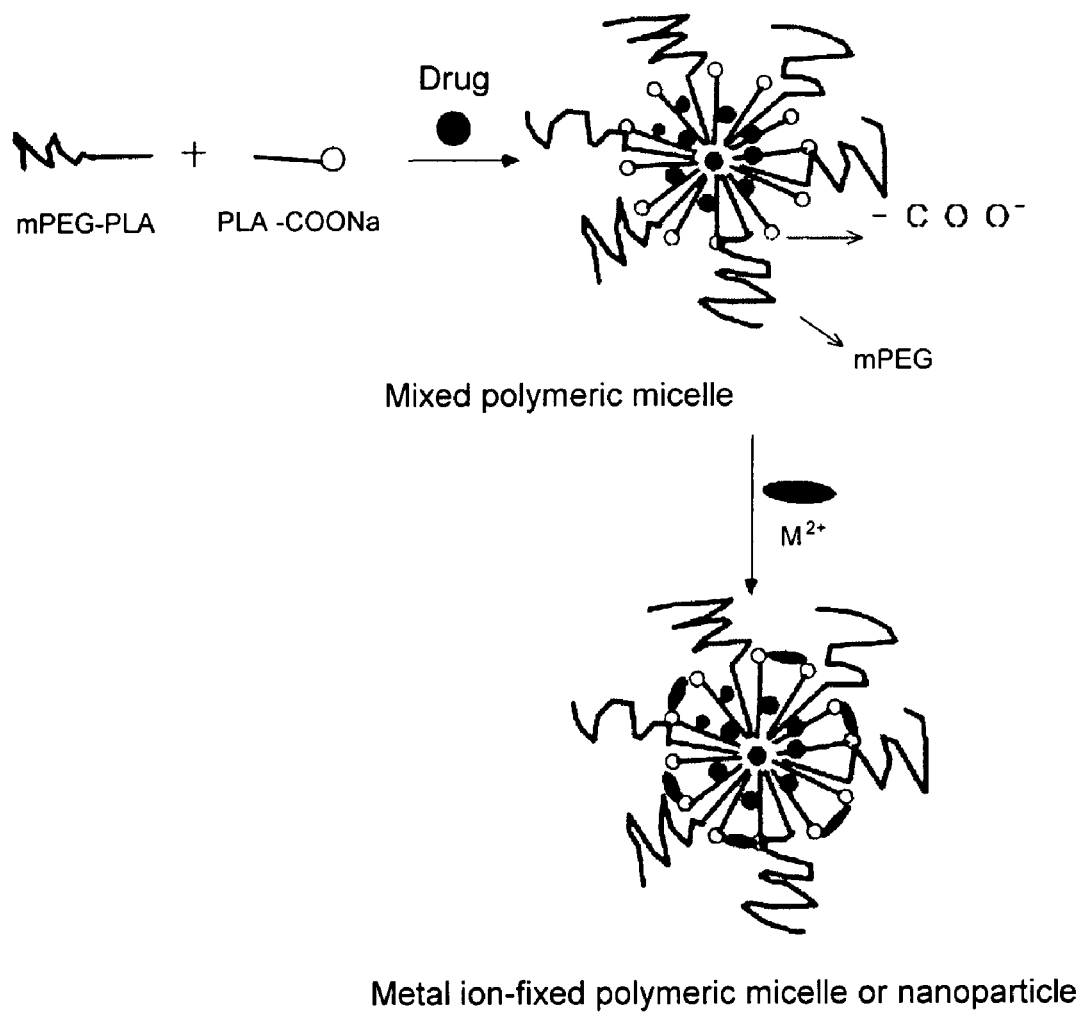
FIG. 5 is a schematic diagram of a $Ca^{2+}$-fixed polymeric micelle containing a hydrophobic drug trapped within the hydrophobic core of the micelle.

As illustrated in FIGS. 4 and 5, when a monovalent metal ion at the carboxyl terminus of the polylactic acid derivative is substituted with a di- or tri-valent metal ion to form a metal ionic bond, the micelles or nanoparticles formed have improved stability.

Either polymeric micelles or nanoparticles can be prepared by changing the equivalents of the metal ion added. Specifically, if a divalent metal ion is added at 0.5 equivalents or less with respect to the carboxyl terminal groups, the metal ion that can form bonds with the carboxyl terminal group of the polylactic acid derivative is insufficient, and thus, polymeric micelles are formed. If a divalent metal ion is added at 0.5 equivalents or more, the metal ion that can form bonds with the carboxyl terminal group of the polylactic acid derivative and is sufficient to firmly fix the micelles, and thus, nanoparticles are formed.

In addition, the drug release rate from the polymeric micelles or nanoparticles may be adjusted by changing the amount of equivalents of the metal ion added. If the metal ion is present at 1 equivalent or less with respect to that of the carboxyl group of the polylactic acid derivative, the number available to bond to the carboxyl terminal group of the polylactic acid derivative is decreased, and so the drug release rate is increased. If the metal ion is present at 1 equivalent or more, the number available to bond to the carboxyl terminal group of the polylactic acid derivative is increased, and so the drug release rate is decreased. Therefore, to increase the drug release rate in the blood, fewer equivalents of the metal ion are used, and to decrease the drug release rate, more equivalents of the metal ion are used.

The metal ion-fixed polymeric compositions of the present invention may contain 5 to 95 wt % of the amphiphilic block copolymer, 5 to 95 wt % of the polylactic acid derivative and 0.01 to 10 equivalents of the di- or tri-valent metal ion with respect to the number of equivalents of carboxyl terminal groups of the polylactic acid derivatives. Preferably, they contain 20 to 80 wt % of the amphiphilic block copolymer, 20 to 80 wt % of the polylactic acid derivative and 0.1 to 5 equivalents of the di- or tri-valent metal ion, and more preferably, 20 to 60 wt % of the amphiphilic block copolymer, 40 to 80 wt % of the polylactic acid derivative and 0.2 to 2 equivalents of the di- or tri-valent metal ion.

The present invention also relates to a pharmaceutical composition containing polymeric micelles or nanoparticles formed from the polymeric compositions of the present invention having a poorly water-soluble drug entrapped therein. The pharmaceutical compositions of the present invention provide for increased plasma concentrations of hydrophobic drugs and can be used in various pharmaceutical formulations.

As shown in FIGS. 3 to 5, a poorly water-soluble drug is mixed with a polymeric composition of an amphiphilic block copolymer and a polylactic acid derivative to form polymeric micelles containing the drug therein. In order to improve its stability, a di- or tri-valent metal ion may be added to form a metal ionic bond with the carboxyl terminal group of the polylactic acid derivative and thereby form drug-containing polymeric micelles and nanoparticles.

The term "poorly water-soluble drugs" or "hydrophobic drugs", refers to any drug or bioactive agent which has a water solubility of 50 mg/ml or less. This includes anticancer agents, antibiotics, anti-inflammatory agents, anesthetics, hormones, antihypertensive agents, agents for the treatment of diabetes, antihyperlipidemic agents, antiviral agents, agents for the treatment of Parkinson's disease, antidementia agents, antiemetics, immunosuppressants, antiulcerative agents, laxatives, and antimalarial agents. Examples of hydrophobic drugs include anticancer agents such as paclitaxel, camptothecin, etoposide, doxorubicin, dausorubicin, idarubicin, ara-C, etc., immunosuppressants such as cyclosporine A, etc. Steroidal hormones such as testosterone, estradiol, estrogen, progesterone, triamcinolon acetate, dexamethasone, etc. and anti-inflammatory agents such as tenoxicam, pyroxicam, indomethacin, COX-II inhibitors, etc., which have a very fast excretion rate from the blood, are also examples of suitable hydrophobic drugs that can be used in the present invention.

The content of the poorly water-soluble drug is preferably within the range of 0.1 to 30 wt % based on the total weight of the pharmaceutical compositions comprising an amphiphilic block copolymer, a polylactic acid derivative, and a hydrophobic drug. The size of the drug-containing polymeric micelles or nanoparticles may be adjusted to be from 5 to 400 nm, preferably, from 10 to 200 nm, depending on the molecular weight of the polymers and the ratio of the amphiphilic block copolymer to the polylactic acid derivative.

For oral or parenteral administration of a poorly water-soluble drug, the drug is entrapped in the polymeric micelles or nanoparticles and is thereby solubilized. Particularly, the metal ion-fixed polymeric micelles or nanoparticles are retained in the bloodstream for a long period of time and accumulate in the target lesions. The drug is released from the hydrophobic core of the micelles to exhibit a pharmacological effect while the micelles are degraded.

For parenteral delivery, the drug may be administered intravenously, intramuscularly, intraperitoneally, transnasally, intrarectally, intraocularly, or intrapulmonarily. For oral delivery, the drug is mixed with the polymeric micelles of the present invention, and then, administered in the form of a tablet, capsule, or aqueous solution.

The metal ion-fixed polymeric micelles or nanoparticles according to the present invention have excellent stability, and thus, can increase the plasma concentration of a drug. As shown in the following Experiments and FIG. 6, Composition 1 wherein paclitaxel is entrapped within the metal ion-fixed polymeric micelles has a longer retention time of drug in the bloodstream, and so maintains an effective plasma drug concentration for a longer period of time compared with Composition 3 wherein paclitaxel is entrapped in the polymeric composition composed of the block copolymer only, and Composition 2 wherein paclitaxel is entrapped in mixed polymeric micelles of the block copolymer and the polylactic acid.

As shown in the following Experiments and FIGS. 7 and 8, Composition 4, wherein paclitaxel is entrapped in the metal ion-fixed polymeric composition, has a longer retention time of drug in the bloodstream, and so maintains an effective plasma drug concentration for a longer period of time as compared with the marketed paclitaxel formulation, Taxol® (Composition 5), a polysorbate ethanol formulation (Composition 6) and has a high inhibition rate on cancer growth and so exhibits high anticancer activity.

Furthermore, the present invention includes a process for preparing the above pharmaceutical composition. Specifically, as shown in FIGS. 3 and 5, the amphiphilic block copolymer, the polylactic acid derivative, and the poorly water-soluble drug are dissolved in an organic solvent, and then, the organic solvent is evaporated therefrom. Thereafter, the obtained mixture is added to an aqueous solution to prepare mixed polymeric micelles containing the poorly water-soluble drug. The metal ion-fixed polymeric micelles or nanoparticles are prepared by adding a di- or tri-valent metal ion to the mixed polymeric micelles thereby fixing the carboxyl terminal group of the polylactic acid derivative.

The polylactic acid derivative, the amphiphilic block copolymer, and the poorly water-soluble drug at a certain ratio can be dissolved in one or more mixed solvents selected from the group consisting of acetone, ethanol, methanol, ethyl acetate, acetonitrile, methylene chloride, chloroform, acetic acid and dioxane. The organic solvent can be removed therefrom to prepare a homogenous mixture of the poorly water-soluble drug and the polymer. The homogenous mixture of the poorly water-soluble drug and the polymeric composition of the present invention can be added to an aqueous solution of pH 4 to 8, at 0 to 80° C. resulting in an aqueous solution of poorly water-soluble drug-containing mixed polymeric micelles. The above drug-containing polymeric micelle aqueous solution can then be lyophilized to prepare the polymeric micelle composition in the form of solid.

An aqueous solution containing 0.001 to 2 M of the, di- or tri-valent metal ion is added to the poorly water-soluble drug-containing mixed polymeric micelle aqueous solution. The mixture is slowly stirred at room temperature for 0.1 to 1 hour and then lyophilized to prepare the metal ion-fixed polymeric micelle or nanoparticle composition in the form of solid.

The following examples will enable those skilled; in the art to more clearly understand how to practice the present invention. It is to be understood that, while the invention has been described in conjunction with the preferred specific embodiments thereof, that which follows is intended to illustrate and not limit the scope of the invention. Other aspects of the invention will be apparent to those skilled in the art to which the invention pertains.

EXAMPLES

Preparations 1-11

Synthesis of Polylactic Acid Derivatives

The polymer was prepared by the polymerization of a 2-hydroxycarboxylic acid derivative in the absence of a catalyst, at an elevated temperature (100 to 200° C.) and under reduced pressure (100 to 0.1 mmHg) for 6 to 24 hours, followed by purification.

Preparation 1

Synthesis 1 of D,L-polylactic Acid (PLA-COOH)

One hundred grams of D,L-lactic acid were introduced into a 250 ml three-neck round-bottomed flask. The flask was equipped with a stirrer, and heated in an oil bath to 80° C. The reaction was performed for 1 hour with the pressure reduced to 25 mmHg by a vacuum a spirator to remove excessive moisture. The reaction was then performed at a temperature of 150° C. under a reduced pressure of 25 mmHg for 6 hours. The resulting product was added to 1 liter of distilled water to precipitate the polymer. The precipitated polymer was then added to distilled water to remove the low molecular weight polymer that was soluble in an aqueous solution of pH 4 or less. The precipitated polymer was then added to 1 liter of distilled water, and the pH of the aqueous solution was adjusted to 6 to 8 by addition of sodium hydrogen carbonate portionwise thereto to dissolve the polymer. The water-insoluble polymer was separated and removed by centrifugation or filtration. A 1 N hydrochloric acid solution was added dropwise thereto and the polymer was precipitated in the aqueous solution. The precipitated polymer was washed twice with distilled water, isolated and dried under reduced pressure to obtain a highly viscous liquid (78 g of D,L-polylactic acid, yield: 78%). The number average molecular weight of the polymer was 540 Daltons as determined by $^1$H-NMR spectrum assay.

Preparations 2-4

Synthesis 2 of D,L-polylactic Acid (PLA-COOH)

D,L-polylactic acid was obtained according to the same procedure as in Preparation 1 except for control of the reaction temperature, pressure, and time as set forth in Table 1. The number average molecular weight and the yield of D,L-polylactic acid synthesized from the above Preparations 1 to 4 are shown in the following Table 1.

TABLE 1

| Preparation | Temperature (° C.) | Time (hours) | Pressure (mmHg) | Mn | Yield (%) |
|---|---|---|---|---|---|
| 1 | 150 | 6 | 25 | 540 | 78 |
| 2 | 160 | 12 | 10 | 1140 | 83 |
| 3 | 160 | 24 | 10 | 1550 | 84 |
| 4 | 160 | 24 | 5 | 2100 | 87 |

*Yield = (Obtained polymer/Used monomer) × 100

Preparation 5

Synthesis 1 of the Copolymer of D,L-lactic Acid and Glycolic Acid (PLGA-COOH)

Fifty-five grams of D,L-lactic acid(0.6 moles) and 45 grams glycolic acid(0.6 moles) were introduced together into a 250 ml three-neck round-bottomed flask. The same procedure as in Preparation 1 was carried out except that the reaction was performed at a temperature of 150° C. and under a reduced pressure of 10 mmHg for 12 hours.

Preparation 6

Synthesis 2 of the Copolymer of D,L-lactic Acid and Glycolic Acid (PLGA-COOH)

Seventy-three grams D,L-lactic acid(0.8 moles) and 27 grams glycolic acid(0.35 moles) were introduced together into a 250 ml three-neck round-bottomed flask. The same procedure as in Preparation 1 was carried out except that the reaction was performed at a temperature of 160° C. and under a reduced pressure of 10 mmHg for 12 hours.

Preparation 7

Synthesis 3 of the Copolymer of D,L-lactic Acid and Glycolic Acid (PLGA-COOH)

Ninety-one grams D,L-lactic acid(1.0 mole) and 9 grams glycolic acid(0.12 moles) were introduced together into a 250 ml three-neck round-bottomed flask. The same procedure as in Preparation 1 was carried out except that the reaction was performed at a temperature of 160° C. and under a reduced pressure of 10 mmHg for 12 hours.

Preparation 8

Synthesis 4 of the Copolymer of D,L-lactic Acid and Glycolic Acid (PLGA-COOH)

Seventy-three grams D,L-lactic acid(0.8 moles) and 27 grams glycolic acid(0.35 moles) were introduced into a 250 ml three-neck round-bottomed flask. The same procedure as in Preparation 1 was carried out except that the reaction was performed at a temperature of 180° C. and under a reduced pressure of 5 mmHg for 24 hours.

The copolymers synthesized in the above Preparations 5 to 8 are shown in Table 2.

TABLE 2

| Preparation | Molar ratio of lactic acid and glycolic acid | | Reaction temperature (° C.) | Reaction time (hrs) | Pressure (mmHg) | Mn (Daltons) | Yield (%) |
|---|---|---|---|---|---|---|---|
| | Reactant | Product | | | | | |
| 5 | 50/50 | 52/48 | 150 | 12 | 10 | 920 | 63 |
| 6 | 70/30 | 67/33 | 160 | 12 | 10 | 1040 | 65 |
| 7 | 90/10 | 91/9 | 160 | 12 | 10 | 1180 | 68 |
| 8 | 70/30 | 71/29 | 180 | 24 | 5 | 1650 | 73 |

Preparation 9

Synthesis of the Copolymer of D,L-lactic Acid and Mandelic Acid (PLMA-COOH)

Seventy-five grams D,L-lactic acid(0.83 moles) and 25 grams D,L-mandelic acid(0.16 moles) were introduced together into a 250 ml three-neck round-bottomed flask. The same procedure as in Preparation 1 was carried out except that the reaction was performed a temperature of 180° C. and under a reduced pressure of 10 to 20 mmHg for 5 hours.

Fifty-four grams (yield: 54%) of a copolymer of D,L-lactic acid and mandelic acid were obtained. The molar ratio of D,L-lactic acid to manidelic acid was 85/15. The number average molecular weight of the polymer was 1,096 Daltons as determined by $^1$H-NMR spectrum assay.

Preparation 10

Synthesis of Acetoxy D,L-polylactic Acid Derivative (AcO—PLA-COOH)

Fifty grams of D,L-polylactic acid (Mn: 1,140 Daltons), synthesized from Preparation 2, and 20 ml of chloracetic acid were introduced together into a 250 ml round-bottomed flask. The flask was equipped with a refrigerator, and the reaction mixture was refluxed under nitrogen flow for 4 hours. Excessive chloracetic acid was removed by distillation, and then, the reaction product was added to a mixture of ice and water. The whole mixture was stirred slowly to precipitate the polymer. The precipitated polymer was separated, washed twice with distilled water, and then, dissolved in anhydrous acetone. Anhydrous magnesium sulfate was added thereto to remove excessive moisture. The product obtained was filtered to remove the magnesium sulfate. Acetone was removed using a vacuum evaporator thereby obtaining liquid acetoxy D,L-polylactic acid (46 g, yield: 92%). By $^1$H-NMR, the acetoxy group was identified as a single peak at 2.02 ppm.

Preparation 11

Synthesis of Palmitoyloxy D,L-polylactic Acid Derivative (PalmO—PLA-COOH)

Twenty grams D,L-polylactic acid (Mn:1,140 Daltons), synthesized from Preparation 2, was introduced into a 250 ml round-bottomed flask. The reactant was completely dehydrated under vacuum in an oil bath of 120° C. The oil bath was cooled to 50° C. and 50 ml acetone was added thereto to completely dissolve the polymer. 5 ml of chloropalmitic acid was added, and the reaction was performed at a temperature of 50° C. for 10 hours under nitrogen. The reaction product was washed with an excessive amount of hexane to remove any residual reactant. The product was then dissolved in acetone and the solution was added to a mixture of ice and water. The whole mixture was stirred slowly resulting in the precipitation of an oligomer. The oligomer was separated and washed twice with distilled water, and then dissolved in anhydrous acetone. Anhydrous magnesium sulfate was added to the solution to remove excessive moisture. The product obtained was filtered to remove the magnesium sulfate. Acetone was removed with a vacuum evaporator thereby obtaining a palmitoyloxy D,L-polylactic acid derivative (19.1 g, yield: 96%). By $^1$H-NMR, the palmitoyl group was identified as peaks of 0.88, 1.3 and 2.38 ppm.

Preparations 12 to 22

Synthesis of Carboxylate Salts of Polylactic Acid Derivatives

The polylactic acid derivatives synthesized from Preparations 1 to 11 were reacted with basic aqueous solutions of sodium hydrogen carbonate, sodium carbonate, potassium hydrogen carbonate, or potassium carbonate, in an acetone solvent, to prepare their carboxylate salts.

Preparation 12

Synthesis 1 of Sodium Salt of Polylactic Acid (PLA-COONa)

D,L-polylactic acid (Mn: 540 Daltons) synthesized from Preparation 1 was dissolved in acetone. The solution was introduced into a round-bottomed flask and the flask was equipped with a stirrer. The solution was stirred slowly at room temperature and a sodium hydrogen carbonate solution (1 N) was slowly added thereto until a pH of 7 was reached. Anhydrous magnesium sulfate was added thereto and excessive moisture was removed therefrom. The mixture obtained was filtered and the acetone was evaporated with a solvent evaporator. A white solid was obtained. The solid was dissolved in anhydrous acetone and the solution was filtered to remove the insoluble portion. Acetone was evaporated leaving the sodium salt of D,L-polylactic acid (yield: 96%) as a white solid. As shown in FIG. 2, a hydrogen peak adjacent to the carboxylic acid group was observed at 4.88 ppm by $^1$H-NMR, and the polymer when dissolved in water had a pH of 6.5 to 7.5.

Preparation 13

Synthesis 2 of the Sodium Salt of polylactic Acid (PLA-COONa)

The sodium salt of polylactic acid (yield: 95%) was synthesized according to the same procedure as in the above Preparation 12 except that D,L-polylactic acid (Mn: 1,140 Daltons) synthesized from Preparation 2 and an aqueous solution of sodium carbonate were used.

Preparation 14

Synthesis of the Sodium Salt of acetoxy-D,L-polylactic Acid (AcO-PLA-COONa)

The sodium salt of acetoxy-D,L-polylactic acid (yield: 95%) was synthesized according to the same procedure as in Preparation 12 except that acetoxy-D,L-polylactic acid (Mn: 1,140 Daltons) synthesized from Preparation 10 and an aqueous solution of sodium carbonate were used.

Preparation 15

Synthesis 1 of Sodium Salt of Palmitoyloxy D,L-polylactic Acid (PalmO—PLA-COONa)

The palmitoyloxy D,L-polylactic acid (Mn: 1,140 Daltons) synthesized from Preparation 11 was completely dissolved in an aqueous solution o f acetone (28.6v/v %). The solution was introduced into a round-bottomed flask and the flask was equipped with a stirrer. The solution was stirred slowly at room temperature, and then, an aqueous solution of sodium hydrogen carbonate (1 N) was added thereto for neutralization. The solution was stirred slowly at room temperature and sodium hydrogen carbonate solution (1 N) was slowly added thereto until a pH of 7 was reached. Anhydrous magnesium sulfate was added thereto to remove excessive moisture. The solution obtained was filtered and the acetone was evaporated with a solvent evaporator. A white solid was obtained. The solid was dissolved in acetone and the solution was filtered to remove any particles that were insoluble in acetone. The acetone was evaporated and the sodium salt of palmitoyloxy D,L-polylactic acid was obtained as a white solid (yield: 96%).

Preparation 16

Synthesis 2 of the Potassium Salt of Polylactic Acid (PLA-COOK)

The potassium salt of polylactic acid (yield: 98%) was synthesized according to the same procedure as in Preparation 12 except that D,L-lactic acid (Mn: 1,550 Daltons) synthesized from Preparation 3 and an aqueous solution of potassium hydrogen carbonate were used.

Preparation 17

Synthesis 3 of the Sodium Salt of Polylactic Acid (PLA-COONa)

The sodium salt of polylactic acid (yield: 95%) was synthesized according to the same procedure as in Preparation 12 except that D,L-lactic acid (Mn: 2,100 Daltons) synthesized from Preparation 4 was used.

Preparation 18

Synthesis 1 of the Sodium Salt of a Copolymer of D,L-lactic Acid and Glycolic Acid (PLGA-COONa)

The sodium salt of a copolymer of D,L-lactic acid and glycolic acid (yield: 98%) was synthesized according to the same procedure as in Preparation 12 except that a copolymer of D,L-lactic acid and glycolic acid (Mn: 920 Daltons) synthesized from Preparation 5 and an aqueous solution of sodium carbonate were used.

Preparation 19

Synthesis 2 of the Sodium Salt of a Copolymer of D,L-lactic Acid and Glycolic Acid (PLGA-COONa)

The sodium salt of a copolymer of D,L-lactic acid and glycolic acid (yield: 93%) was synthesized according to the same procedure as in Preparation 12 except that a copolymer of D,L-lactic acid and glycolic acid (Mn: 1,040 Daltons) synthesized from Preparation 6 was used.

Preparation 20

Synthesis of the Potassium Salt of a Copolymer of D,L-lactic Acid and Glycolic Acid (PLGA-COOK)

The potassium salt of a copolymer of D,L-lactic acid and glycolic acid (yield: 92%) was synthesized according to the same procedure as in Preparation 12 except that a copolymer of D,L-lactic acid and glycolic acid (Mn: 1,180 Daltons) synthesized from Preparation 7 and an aqueous solution of potassium carbonate were used.

Preparation 21

Synthesis 3 of the Sodium Salt of a Copolymer of D,L-lactic Acid and Glycolic Acid (PLGA-COONa)

The sodium salt of a copolymer of D,L-lactic acid and glycolic acid (yield: 98%) was synthesized according to the same procedure as in Preparation 12 except that a copolymer of D,L-lactic acid and glycolic acid (Mn: 1,650 Daltons) synthesized from Preparation 8 was used.

Preparation 22

Synthesis of the Sodium Salt of a Copolymer of D,L-lactic Acid and Mandelic Acid (PLMA-COONa)

The sodium salt of a copolymer of D,L-lactic acid and mandelic acid (yield: 96%) was synthesized as white solid according to the same procedure as in Preparation 12 except that a copolymer of D,L-lactic acid and mandelic acid synthesized from Preparation 9 (Mn: 1,096 Daltons) was used.

The carboxylate salts of the polylactic acid derivatives synthesized from the above Preparations 12 to 22 are shown in Table 3.

TABLE 3

| Preparation | Reactant (MN) | Base | Product | Mn (Daltons) | Yield (%) |
|---|---|---|---|---|---|
| 12 | PLA-COOH (540) | NaHCO$_3$ | PLA-COONa | 540 | 96 |
| 13 | PLA-COOH (1,140) | Na$_2$CO$_3$ | PLA-COONa | 1,140 | 95 |
| 14 | AcO-PLA-COOH (1,140) | Na$_2$CO$_3$ | AcO-PLA-COONa | 1,140 | 95 |
| 15 | PalmitoylO-PLA-COOH (1,140) | NaHCO$_3$ | PalmitoylO-PLA-COONa | 1,140 | 96 |
| 16 | PLA-COOH (1,550) | KHCO$_3$ | PLA-COOK | 1,550 | 98 |
| 17 | PLA-COOH (2,100) | NaHCO$_3$ | PLA-COONa | 2,100 | 95 |
| 18 | PLGA-COOH (920) | Na$_2$CO$_3$ | PLGA-COONa | 920 | 98 |
| 19 | PLGA-COOH (1,040) | NaHCO$_3$ | PLGA-COONa | 1,040 | 93 |
| 20 | PLGA-COOH (1,180) | K$_2$CO$_3$ | PLGA-COOK | 1,180 | 92 |

TABLE 3-continued

| Preparation | Reactant (MN) | Base | Product | Mn (Daltons) | Yield (%) |
|---|---|---|---|---|---|
| 21 | PLGA-COOH (1,650) | NaHCO₃ | PLGA-COONa | 1,650 | 98 |
| 22 | PLMA-COOH (1,096) | NaHCO₃ | PLMA-COONa | 1,096 | 96 |

Preparations 23 to 29

Synthesis of an AB Type Block Copolymer Composed of a Hydrophilic A Block and a Hydrophobic B Block Preparation 23

Polymerization of a Monomethoxypolyethylene Glycol-polylactide (mPEG-PLA) Block Copolymer (AB Type)

Five grams of monomethoxypolyethylene glycol (Mn: 2,000 Daltons) was introduced into a 100 ml two-neck round-bottomed flask, and dehydrated by heating to 130° C. under a reduced pressure (1 mmHg) for 3 to 4 hours. The reaction flask was filled with dried nitrogen and a reaction catalyst, stannous octoate (Sn(Oct)$_2$), was injected with 0.1 wt % (10.13 mg, 25 mmol) of D,L-lactide using a syringe. The reaction mixture was stirred for 30 minutes, the pressure was reduced to 1 mmHg at 130° C. for 1 hour to remove the solvent (toluene) dissolving the catalyst. Purified lactide (10.13 g) was added thereto, and the mixture was heated to 130° C. for 18 hours. The polymer formed was dissolved in methylene chloride, and diethyl ether was added thereto to precipitate the polymer. The polymer obtained was dried in a vacuum oven for 48 hours. The mPEG-PLA obtained had the number average molecular weight of 2,000-1,765 Daltons, and was confirmed to be of the AB type by $^1$H-NMR.

Preparation 24

Polymerization of a Monomethoxypolyethylene Glycol-polylactide (mPEG-PLA) Block Copolymer (AB type)

Five grams of monomethoxypolyethylene glycol (Mn: 2,000 Daltons) was introduced into a 100 ml two-neck round-bottomed flask, and dehydrated by heating to 130° C. under a reduced pressure (1 mmHg) for 3 to 4 hours. The reaction flask was filled with dried nitrogen and a reaction catalyst, stannous octoate (Sn(Oct)$_2$), was injected with 0.1 wt % (13.75 mg, 34 mmol) of D,L-lactide using a syringe. The reaction mixture was stirred for 30 minutes, the pressure was reduced to 1 mmHg at 130° C. for 1 hour to remove the solvent (toluene) dissolving the catalyst. Purified lactide (13.75 g) was added thereto, and the mixture was heated to 130° C. for 18 hours. The polymer formed was dissolved in methylene chloride, and diethyl ether was added thereto to precipitate the polymer. The polymer obtained was dried in a vacuum oven for 48 hours. The mPEG-PLA obtained had a number average molecular weight of 2,000-5,000 Daltons, and was confirmed to be of the AB type by $^1$H-NMR.

Preparation 25

Polymerization of a Monomethoxypolyethylene Glycol-polylactide (mPEG-PLA) Block Copolymer (AB Type)

Five grams of monomethoxypolyethylene glycol (Mn: 2,000 Daltons) was introduced into a 100 ml two-neck round-bottomed flask, and dehydrated by heating to 130° C. under a reduced pressure (1 mmHg) for 3 to 4 hours. The reaction flask was filled with dried nitrogen and a reaction catalyst, stannous octoate (Sn(Oct)$_2$), was injected with 0.1 wt % (22.0 mg, 55 mmol) of D,L-lactide using a syringe. The reaction mixture was stirred for 30 minutes, the pressure was reduced to 1 mmHg at 130° C. for 1 hour to remove the solvent (toluene) dissolving the catalyst. Purified lactide (22 g) was added thereto, and the mixture was heated to 130° C. for 18 hours. The polymer formed was dissolved in methylene chloride, and diethyl ether was added thereto to precipitate the polymer. The polymer obtained was dried in a vacuum oven for 48 hours. The mPEG-PLA obtained had a number average molecular weight of 2,000-8,000 Daltons, and was confirmed to be of the AB type by $^1$H-NMR.

Preparation 26

Polymerization of a Monomethoxypolyethylene Glycol-poly(lactic-co-glycolide) (mPEG-PLGA) Block Copolymer (AB Type)

To synthesize the mPEG-PLGA block copolymer, monomethoxypolyethylene glycol (Mn: 5,000 Daltons) was reacted with lactide and glycolide in the presence of the catalyst, stannous octoate, at 120° C. for 12 hours according to the same procedure as in Preparation 23. The mPEG-PLGA obtained had a number average molecular weight of 5,000-4,000 Daltons, and was confirmed to be of the AB type by $^1$H-NMR.

Preparation 27

Polymerization of a Monomethoxypolyethylene Glycol-poly(lactic-co-p-dioxan-2-one) (mPEG-PLDO) Block Copolymer (AB Type)

To synthesize a MPEG-PLDO block copolymer, monomethoxypolyethylene glycol (Mn: 12,000 Daltons) was reacted with lactide and p-dioxan-2-one in the presence of the catalyst, stannous octoate, at 110° C. for 12 hours according to the same procedure as in Preparation 23. The mPEG-PLDO obtained had a number average molecular weight of 12,000-10,000 Daltons, and was confirmed to be of the AB type by $^1$H-NMR.

Preparation 28

Polymerization of a Monomethoxypolyethylene Glycol-polycaprolactone (mPEG-PCL) Block Copolymer (AB Type)

To synthesize a mPEG-PCL block copolymer, monomethoxypolyethylene glycol (Mn: 12,000 Daltons) was reacted with caprolactone in the presence of the catalyst, stannous octoate, at 130° C. for 12 hours, according to the same procedure as in Preparation 23. The mPEG-PCL obtained had a number average molecular weight of 12,000-5,000 Daltons, and was confirmed be of the AB type by $^1$H-NMR.

Preparation 29

Polymerization of a Monomethoxypolyethylene Glycol-polylactide-palmitate (mPEG-PLA-palmitate) Block Copolymer (AB Type)

The synthesized monomethoxypolyethylene glycol-polylactide (mPEG-PLA) (Mn: 2,000-1,750, 20 g) was introduced into a flask and completely dehydrated under vacuum in an oil bath at 120° C. The reactant was cooled to 50° C. and 50 ml of acetone was added thereto in order to completely dissolve the polymer. 2 ml of palmitoyl chloride was added thereto (molar ratio: palmitoyl chloride/mPEG-PLA=1.2/1), and the reaction was performed at 50° C. under nitrogen flow for 10 hours. The reaction mixture was washed with excess hexane to remove any residual reactant. The polymer obtained was dissolved in methylene chloride, precipitated with diethyl ether and then filtered. The polymer obtained was dried in a vacuum oven for 48 hours. The mPEG-PLA-palmitate obtained had a Mn of 2,000-1,800 Daltons. In addition, it was confirmed by $^1$H-NMR that a palmitoyl group was bonded to the —OH terminal group of the MPEG-PLA.

The block copolymers synthesized from the above Preparations 23 to 29 are the following Table 4.

TABLE 4

| Preparation | Amphiphilic block copolymer | Mn (Daltons) | Yield (%) |
|---|---|---|---|
| 23 | mPEG-PLA | 2,000-1,765 | 86 |
| 24 | mPEG-PLA | 2,000-5,000 | 87 |
| 25 | mPEG-PLA | 2,000-8,000 | 85 |
| 26 | mPEG-PLGA | 5,000-4,000 | 90 |
| 27 | mPEG-PLDO | 12,000-10,000 | 78 |
| 28 | mPEG-PCL | 12,000-5,000 | 93 |
| 29 | mPEG-PLA-palmitate | 2,000-1,800 | 90 |

Examples 1 to 7

Preparation of Poorly Water-Soluble Drug-Containing Mixed Polymeric Micelles

Example 1

Preparation of a Paclitaxel-Containing Mixed Polymeric Micelle Composition of D,L-PLA-COONa and mPEG-PLGA Block Copolymers D,L-PLA-COONa (Mn: 1,140 Daltons)(130 mg), synthesized from the above Preparation, an amphiphilic block copolymer mPEG-PLGA (Mn: 5,000-4,000 Daltons)(100 mg), and 40 mg paclitaxel were dissolved in 1 ml of acetone to prepare a clear solution. Acetone was removed therefrom to prepare the paclitaxel-containing mixed polymeric composition. Distilled water(2 ml) was added to the paclitaxel-containing polymeric composition, and the mixture was stirred for 20 minutes at 40° C. to prepare the paclitaxel-containing mixed polymeric micelle aqueous solution. The solution was passed through a filter having a pore size of 200 nm to remove any undissolved paclitaxel. The content and solubility of paclitaxel were determined by HPLC and the particle size was measured by a Dynamic Light Scattering (DLS) Method.

D,L-PLA-COONa/mPEG-PLGA=56/44

Content of paclitaxel: 14.8 wt %

Solubility of paclitaxel in an aqueous solution: 40 mg/ml

Particle size: 24 nm

Example 2

Preparation of a Paclitaxel-Containing Mixed Polymeric Micelle Composition of D,L-PLA-COONa and mPEG-PLA Block Copolymer D,L-PLA-COONa (Mn: 1,140 Daltons)(180 mg), synthesized from the above Preparation, 100 mg of the amphiphilic block copolymer mPEG-PLA (Mn: 2,000-1,765 Daltons), and 20 mg of paclitaxel were dissolved in 1 ml of acetone to prepare a clear solution. Acetone was removed therefrom to prepare a paclitaxel-containing mixed polymeric composition. Distilled water(2 ml) was added to the paclitaxel-containing polymeric composition, and the mixture was stirred for 30 minutes at 40° C. to prepare the paclitaxel-containing mixed polymeric micelle aqueous solution. The solution was passed through a filter having a pore size of 200 nm to remove any undissolved paclitaxel.

D,L-PLA-COONa/mPEG-PLA=64/36

Content of paclitaxel: 6.7 wt %

Solubility of paclitaxel in an aqueous solution: 10 mg/ml

Particle size: 16 nm

Example 3

Preparation of a Cyclosporine A-containing Mixed Polymeric Micelle Composition of D,L-PLGA-COONa and mPEG-PLA Block Copolymers A cyclosporine A-containing mixed polymeric micelle aqueous solution was prepared according to the same procedure as in Example 2 except that 150 mg of D,L-PLGA-COONa (Mn: 1,650 Daltons) synthesized from the above Preparation, 50 mg of the amphiphilic block copolymer MPEG-PLA (Mn: 2,000-,1765 Daltons), and 20 mg of cyclosporine A were used, and passed through a filter having a pore size of 200 nm to remove any undissolved cyclosporine A.

D,L-PLGA-COONa/mPEG-PLA=75/25
Content of cyclosporine A: 9.1 wt %
Particle size: 20 nm Example 4

Preparation of a Cyclosporine A-containing Mixed Polymeric Micelle Composition of D,L-PLA-COONa and mPEG-PLA Block Copolymers A cyclosporine A-containing mixed polymeric micelle aqueous solution was prepared according to the same procedure as in Example 2 except that 100 mg of D,L-PLA-COONa (Mn: 540 Daltons) synthesized from the above Preparation, 100 mg of the amphiphilic block copolymer MPEG-PLA (Mn: 2,000-1,765 Daltons), and 25 mg of cyclosporine A were used.
D,L-PLA-COONa/mPEG-PLA=50/50
Content of cyclosporine A: 11.1 wt %
Particle size: 22 nm Example 5

Preparation of a Cyclosporine A-containing Mixed Polymeric Micelle Composition of D,L-PLGA-COONa and mPEG-PLA Block Copolymers A cyclosporine A-containing mixed polymeric micelle aqueous solution was prepared according to the same procedure as in Example 2 except that 100 mg of D,L-PLGA-COONa (Mn: 1,040 Daltons) synthesized from the above Preparation, 100 mg of the amphiphilic block copolymer mPEG-PLA (Mn: 2,000-,1765 Daltons), and 25 mg of cyclosporine A were used.
D,L-PLGA-COONa/mPEG-PLA=50/50
Content of cyclosporine A: 11.1 wt %
Particle size: 24 nm Example 6

Preparation of a Paclitaxel-containing Mixed Polymeric Micelle Composition of D,L-PLA-COONa and mPEG-PLA Block Copolymer A paclitaxel-containing mixed polymeric micelle aqueous solution was prepared according to the same procedure as in Example 2 except that D,L-PLA-COONa (Mn: 1,140 Daltons)(100 mg), synthesized from the above Preparation, 90 mg of the amphiphilic block copolymer mPEG-PLA (Mn: 2,000-5,000 Daltons), and 10 mg of paclitaxel were used.
D,L-PLA-COONa/mPEG-PLA=54/46
Content of paclitaxel: 5.0 wt %
Solubility of paclitaxel in an aqueous solution: 10 mg/ml
Particle size: 56 nm Example 7

Preparation of a Paclitaxel-containing Mixed Polymeric Micelle Composition of D,L-PLA-COONa and mPEG-PLA Block Copolymer A paclitaxel-containing mixed polymeric micelle aqueous solution was prepared according to the same procedure as in Example 2 except that D,L-PLA-COONa (Mn: 1,140 Daltons)(150 mg), synthesized from the above Preparation, 90 mg of the amphiphilic block copolymer mPEG-PLA (Mn: 2,000-8,000 Daltons), and 10 mg of paclitaxel were used.
D,L-PLA-COONa/mPEG-PLA=63/37
Content of paclitaxel: 4.0 wt %
Solubility of paclitaxel in an aqueous solution: 10 mg/ml
Particle size: 56 nm Comparative Example 1

Preparation of Paclitaxel-containing Polymeric Micelles of D,L-PLA-COONa

D,L-PLA-COONa (Mn: 1,140 Daltons)(80 mg) synthesized from the above Preparation and 20 mg of paclitaxel were dissolved in 1 ml of acetone. The acetone was removed using a vacuum evaporator and distilled water was added thereto to prepare paclitaxel-containing D,L-PLA-COONa polymeric micelles. The mixture obtained was passed through a filter having a pore size of 200 nm to remove any undissolved paclitaxel. The content and solubility of paclitaxel, and particle size were as follows:
Content of paclitaxel: 20 wt %
Solubility of paclitaxel in an aqueous solution: 20 mg/ml
Particle size: 18 nm Comparative Example 2

Preparation of Paclitaxel-containing mPEG-PLGA Polymeric Micelles mPEG-PLGA (Mn: 5,000-4,000 Daltons)(80 mg) synthesized from the above Preparation and 20 mg of paclitaxel were dissolved in 1 ml of acetone. The acetone was removed using a vacuum evaporator and distilled water was added thereto to prepare paclitaxel-containing mPEG-PLGA polymeric micelles.
Content of paclitaxel: 5 wt %
Solubility of paclitaxel in an aqueous solution: 5 mg/ml
Particle size: 28 nm Experimental Example 1

Stability Test

The drug loading efficiency and stability at 37° C. of an aqueous solution of the paclitaxel-containing mixed polymeric micelle composition obtained from Example 1 was compared with that of the D,L-PLA-COONa polymeric micelle composition obtained from Comparative Example 1 and the mPEG-PLGA polymeric micelle composition obtained from Comparative Example 2. The drug loading efficiency of the polymeric micelles was calculated by preparing polymeric micelles containing excessive drug, passing them through a filter having a pore size of 200 nm, measuring the drug concentration in the filtrate by HPLC, and reducing the measured concentration to weight % of the drug on the basis of the total weight of the polymeric micelle composition. The results are shown in Table 5.

TABLE 5

|  | Example 1 | Comparative Example 1 | Comparative Example 2 |
|---|---|---|---|
| Loading efficiency (%) | 14.8 | 20 | 5 |

FIGS. 1 to 3 are schematic diagrams of the polymeric micelles of the above Example 1 and Comparative Examples 1 and 2.

As shown in Table 5, the loading efficiency of paclitaxel was 14.8 wt % in the mixed polymeric micelles and 20 wt % in the D,L-PLA-COONa polymeric micelles, whereas it was only 5 wt % in the mPEG-PLGA polymeric micelles. Consequently, it was demonstrated that the mPEG-PLGA polymeric micelles had only about ⅓ of the loading efficiency as compared with other polymeric micelles, and the mixed polymeric micelles of the present invention had a loading efficiency similar to the D,L-PLA-COONa.

The polymeric micelles were diluted in a phosphate buffered saline solution with a pH of 7 to adjust the concentration of paclitaxel to 1 mg/ml. Then, the concentration of paclitaxel was measured at time intervals while incubating at 37° C. The results are shown in Table 6.

TABLE 6

Stability of mixed and single polymeric micelles at 37° C.

| | Concentration of paclitaxel (mg/ml) | | |
|---|---|---|---|
| Hours | Example 1 | Comparative Example 1 | Comparative Example 2 |
| 0 | 1.0 | 1.0 | 1.0 |
| 1 | 1.0 | 0.6 | 1.0 |
| 6 | 1.0 | 0.4 | 0.9 |
| 12 | 1.0 | 0.3 | 0.5 |
| 24 | 1.0 | 0.3 | 0.4 |

As shown in Table 6, paclitaxel was not released within 24 hours from the mixed polymeric micelle composition of Example 1. In contrast, paclitaxel was released in a burst after 1 hour from the D,L-PLA-COONa polymeric micelle composition of Comparative Example 1 and after 6 hours from the mPEG-PLGA polymeric micelle composition of Comparative Example 2. Only about 40% of the drug remained after 24 hours in the mPEG-PLGA polymeric micelle composition of Comparative Example 2. The above results demonstrate that the mixed polymeric micelle composition of the present invention has stability comparable to the mPEG-PLGA polymeric micelle composition of Comparative Example 2.

Experimental Example 2

Evaluation of the Effect of the Composition Ratio of the Polymers to the Stability of Poorly Water-Soluble Drug-Containing Mixed Polymeric Micelles Compositions containing 9.1 wt % of paclitaxel, on the basis of the total weight of the composition, were prepared according to the procedure in Example 1. The composition ratios of D,L-PLA-COONa (Mn: 1,140 Daltons) to mPEG-PLA (Mn: 2,000-1,765 Daltons) were changed as follows: 0/100, 10/90, 20/80, 40/60, 50/50, 60/40, 80/20, 90/10, and 100/0. The compositions were then diluted in a phosphate buffered solution at a pH of 7 to adjust the concentration of paclitaxel to 1 mg/ml. The concentration of paclitaxel was measured at time intervals while incubating at 25° C. to compare the micelle stability. The results are shown in Table 7.

TABLE 7

Comparison of the stability at 25° C. depending on the composition ratio of the polylactic acid derivative and the amphiphilic block copolymer

| D,L-PLA-COONa (mg) | mPEG-PLA (mg) | Paclitaxel (mg) | Initial Conc. (mg/ml) | Conc. after 12 hrs (mg/ml) | Conc. after 24 hrs (mg/ml) |
|---|---|---|---|---|---|
| — | 100 | 10 | 1.0 | 0.65 | 0.2 |
| 10 | 90 | 10 | 1.0 | 1.0 | 0.83 |
| 20 | 80 | 10 | 1.0 | 1.0 | 1.0 |
| 40 | 60 | 10 | 1.0 | 1.0 | 1.0 |
| 50 | 50 | 10 | 1.0 | 1.0 | 1.0 |
| 60 | 40 | 10 | 1.0 | 1.0 | 1.0 |
| 80 | 20 | 10 | 1.0 | 1.0 | 1.0 |
| 90 | 10 | 10 | 1.0 | 1.0 | 0.94 |
| 100 | — | 10 | 1.0 | 0.37 | 0.32 |

As shown in Table 7, the mixed polymeric micelles of the present invention had a constant paclitaxel concentration even after 24 hours, while the single polymeric micelles comprising a polylactic acid derivative or an amphiphilic block copolymer had a decreased paclitaxel concentration after 12 hours. Consequently, it was demonstrated that the mixed polymeric micelles had better stability than the single polymeric micelles.

Examples 8 to 13

Preparation of Di- or Tri-valent Metal Ion-fixed Poorly Water-soluble Drug-containing Micelles or Nanoparticles Example 8

Preparation of $Ca^{2+}$-fixed Paclitaxel-containing Micelles of D,L-PLA-COONa and MPEG-PLA Block Copolymers Step 1: Preparation of Paclitaxel-containing Polymeric Micelles of D,L-PLA-COONa and mPEG-PLA Block Copolymers For this step, 130 mg (114 mmol) of D,L-PLA-COONa (Mn: 1,140) of Preparation 13, 30 mg of paclitaxel, and 100 mg of mPEG-PLA (Mn: 2,000-1,765 Daltons) of Preparation 23 were completely dissolved in 2 ml of acetone to obtain a clear solution. Acetone was removed therefrom to prepare a paclitaxel-containing polymeric composition. Distilled water (2.5 ml) was added thereto and the mixture was stirred for 30 minutes at 40° C. to prepare the paclitaxel-containing polymeric micelle aqueous solution.

Step 2: Fixation with the Divalent Metal Ion

For this step, 0.29 ml (58 mmol) of a 0.2 M aqueous solution of anhydrous calcium chloride was added to the polymeric micelle aqueous solution prepared in Step 1, and the mixture was stirred for 20 minutes at room temperature. The mixture was passed through a filter having a pore size of 200 nm, and then was lyophilized. The content and solubility of paclitaxel were measured by HPLC and the particle size was measured according to a Dynamic Light Scattering (DLS) Method.

D,L-PLA-COONa/mPEG-PLA (weight ratio): 56.5/43.5
Content of paclitaxel: 11.5 wt %
Solubility of paclitaxel in the aqueous solution: 10.7 mg/ml
Particle size: 18 nm Example 9

Preparation of $Mg^{2+}$-fixed Paclitaxel-containing Polymeric Micelles of D,L-PLA-COONa and mPEG-PLA Block Copolymers In this example, 0.29 ml (58 mmol) of a 0.2 M anhydrous magnesium chloride aqueous solution was added to the polymeric micelle aqueous solution prepared in Step 1 of the above Example 8 and the mixture was stirred for 20 minutes at room temperature. The mixture was passed through a filter having a pore size of 200 nm, and then was lyophilized.
D,L-PLA-COONa/mPEG-PLA (weight ratio): 56.5/43.5
Content of paclitaxel: 11.5 wt %
Solubility of paclitaxel in the aqueous solution: 10.7 mg/ml
Particle size: 18 nm Example 10

Preparation of $Zn^{2+}$-fixed Paclitaxel-containing Polymeric Micelles of D,L-PLA-COONa and mPEG-PLA Block Copolymer In this example, 0.29 ml (58 mmol) of a 0.2 M anhydrous zinc chloride aqueous solution was added to the polymeric micelle aqueous solution prepared in Step 1 of the above Example 8, and the mixture was stirred for 20 minutes at room temperature. The mixture was passed through a filter having a pore size of 200 nm, and then was lyophilized.
D,L-PLA-COONa/mPEG-PLA (weight ratio): 56.5/43.5
Content of paclitaxel: 11.5 wt %
Solubility of paclitaxel in the aqueous solution: 10.7 mg/ml
Particle size: 18 nm Example 11

Preparation of $Ca^{2+}$-fixed Paclitaxel-containing Polymeric Micelles of D,L-PLMA-COONa and mPEG-PLA-Palmitate Block Copolymers A $Ca^{2+}$-fixed paclitaxel-containing polymeric micelle composition was prepared according to the same procedure as Example 8 except that 130 mg (119 mmol) of D,L-PLMA-COONa (Mn: 1,096) of Preparation 22, 30 mg of paclitaxel, 100 mg of mPEG-PLA-Palmitate (Mn: 2,000-1,800 Daltons) of Preparation 29, and ethanol instead of acetone were used.
D,L-PLMA-COONa/mPEG-PLA-Palmitate (weight ratio): 56.5/43.5
Content of paclitaxel: 11.5 wt %
Solubility of paclitaxel in an aqueous solution: 10.7 mg/ml
Particle size: 18 nm Example 12

Preparation of $Ca^{2+}$-fixed Paclitaxel-containing Polymeric Micelles of D,L-PLA-COONa and mPEG-PLA Block Copolymers A $Ca^{2+}$-fixed paclitaxel-containing polymeric micelle composition was prepared according to the same procedure as Example 8 except that 100 mg (88 mmol) of D,L-PLA-COONa (Mn: 1,140) of Preparation 13, 10 mg of paclitaxel, 90 mg of mPEG-PLA (Mn: 2,000-5,000 Daltons) of Preparation 24, and ethanol instead of acetone were used.
D,L-PLA-COONa/mPEG-PLA (weight ratio): 54/46
Content of paclitaxel: 5.0 wt %
Solubility of paclitaxel in an aqueous solution: 10.0 mg/ml
Particle size: 58 nm Example 13

Preparation of $Ca^{2+}$-fixed Paclitaxel-containing Polymeric Micelles of D,L-PLA-COONa and mPEG-PLA Block Copolymers A $Ca^{2+}$-fixed paclitaxel-containing polymeric micelle composition was prepared according to the same procedure as Example 8 except that 150 mg (132 mmol) of D,L-PLA-COONa (Mn: 1,140) of Preparation 13, 10 mg of paclitaxel, 90 mg of mPEG-PLA (Mn: 2,000-8,000 Daltons) of Preparation 25, and ethanol instead of acetone were used.
D,L-PLA-COONa/mPEG-PLA (weight ratio): 63/37
Content of paclitaxel: 4.0 wt %
Solubility of paclitaxel in an aqueous solution: 10.0 mg/ml
Particle size: 50 nm Experimental Example 3

Evaluation of the Stability of Polymeric Micelle or Nanoparticle Compositions Depending on the Number of Equivalents of a Metal Ion used To evaluate the stability of polymeric micelle or nanoparticle compositions depending on the number of equivalents of metal ion used, polymeric micelle compositions were prepared as follows.

Step 1: Preparation of Paclitaxel-containing Mixed Polymeric Micelles of D,L-PLA-COONa and mPEG-PLA Block Copolymers For this step, 170 mg (149 mmol) of D,L-PLA-COONa (Mn: 1,140), 30 mg of paclitaxel and 50 mg of the amphiphilic block copolymer mPEG-PLA (Mn: 2,000-1,765 Daltons) were dissolved in 2 ml of acetone to obtain a clear solution. Acetone was removed therefrom to prepare a paclitaxel-containing polymeric micelle composition. Distilled water(3 ml) was added to the polymeric micelle composition, and the mixture was stirred for 30 minutes at 40° C. to prepare the paclitaxel-containing polymeric micelle aqueous solution.

Step 2: Fixation with the Divalent Metal Ion

The paclitaxel-containing polymeric micelle aqueous solution prepared in Step 1 was divided into 3 parts, 1 ml per part. To each part was added 0.0625, 0.125, and 0.25 ml (12.5, 25, and 50 mmol) of a 0.2 M anhydrous calcium chloride aqueous solution. The mixture was stirred at room temperature for 20 minutes. The mixture was passed through a filter having a pore size of 200 nm. Then, a phosphate buffer solution of pH 7.4 was added thereto to adjust the concentration of paclitaxel to 1 mg/ml. The concentration of paclitaxel was measured by HPLC while culturing at 37° C. The results are shown in Table 8.

TABLE 8

| | mPEG-PLA/<br>D,L-PLA-COONa | CaCl$_2$/D,L-<br>PLA-COONa | Drug conc. | | | |
|---|---|---|---|---|---|---|
| | (wt. ratio) | (eq.) | 0 hr | 6 hrs | 12 hrs | 24 hrs |
| 0.25 eq. | 50/170 | 0.25/1.00 | 1.0 | 1.0 | 0.9 | 0.7 |
| 0.5 eq. | 50/170 | 0.50/1.00 | 1.0 | 1.0 | 1.0 | 1.0 |
| 1.0 eq. | 50/170 | 1.00/1.00 | 1.0 | 1.0 | 1.0 | 1.0 |
| 0 eq. | 50/170 | 0.00/1.00 | 1.0 | 0.4 | 0.2 | 0.2 |

(eq.: equivalent)

As shown in Table 8, the drug concentration was reduced by 80% compared with the initial concentration and was 0.2 mg/ml after 24 hours when Ca$^{2+}$ was not added. The drug concentration was reduced by about 30% compared with the initial concentration and was 0.7 mg/ml after 24 hours when 0.25 equivalents of Ca$^{2+}$ was added, which was higher than that when Ca$^{2+}$ was not added. Furthermore, the drug concentration was not changed after 24 hours when 0.5 equivalents or more of Ca$^{2+}$ was added. As described above, the Ca$^{2+}$-treated composition is more stable than the non-treated composition, and the stability was remarkably enhanced when 0.5 equivalents or more of Ca$^{2+}$ was added.

Experimental Example 4

Stability Test of the Polymeric Micelles Depending on the M.W. of the D,L-polylactic acid Sodium Salt (D,L-PLA-COONa) used To test the stability of the nanoparticle composition depending on the M.W. of the D,L-polylactic acid sodium salt (D,L-PLA-COONa) used, the polymeric micelle compositions were prepared as follows.

Paclitaxel, mPEG-PLA (Mn: 2,000-1,776), and D,L-PLA-COONa (Mn: 646, 1,145, 1,500 or 2,300) were admixed at an equivalent ratio of 1:3:3, and then the mixture was dissolved in 5 ml of anhydrous ethanol to prepare a clear solution. Ethanol was removed therefrom using vacuum evaporator to prepare a paclitaxel-containing polymeric composition. Distilled water(12 ml) was added thereto and the mixture was stirred for 10 minutes at 60° C. to prepare a paclitaxel-containing polymeric micelle aqueous solution. To the above polymeric micelle solution was added a CaCl$_2$ aqueous solution (concentration: 100 mg/ml) of the same number of equivalents as the D,L-PLA-COONa, and the mixture was stirred for 20 minutes at room temperature. The mixture was passed through a filter with a pore size of 200 nm, and then a phosphate buffer solution of pH 7.4 was added thereto to dilute the mixture to have 1 mg/ml of paclitaxel. The mixture was allowed to stand at 37° C. and the concentration of paclitaxel over the lapse of time was measured by HPLC. The results are shown in Table 9.

As shown in Table 9, as the M.W. of D,L-PLA-COONa was increased to 646, 1,145, 1,500, and 2,300, the drug concentration after 14 days was increased to 0.15, 0.23, 0.36 and 0.62 mg/ml, respectively. As the M.W of D,L-PLA-COONa was increased, drug precipitation was decreased, which demonstrated that the polymeric micelle composition was relatively more stabilized.

Experimental Example 5

Stability Test of the Polymeric Micelles Depending on the Number of Equivalents of D,L-polylactic acid Sodium Salt (D,L-PLA-COONa) used To test the stability of the nanoparticle composition depending on the number of equivalents of D,L-polylactic acid sodium salt (D,L-PLA-COONa) used, the polymeric micelle compositions were prepared as follows.

Paclitaxel, mPEG-PLA (Mn: 2,000-1,776), and D,L-PLA-COONa (Mn: 646, 1,145) were admixed in an equivalent ratio of 1:2:x wherein x is 2, 4, 6, 8, 10 or 12, and then the mixture was dissolved in 5 ml of anhydrous ethanol to prepare a clear solution. Ethanol was removed therefrom using vacuum evaporator to prepare a paclitaxel-containing polymeric composition. Distilled water(12 ml) was added thereto and the mixture was stirred for 10 minutes at 60° C. to prepare the polymeric micelle aqueous solution containing paclitaxel. To the above polymeric micelle solution was added a CaCl$_2$ aqueous solution (concentration: 100 mg/ml) of the same number of equivalents as the D,L-PLA-COONa, and the mixture was stirred for 20 minutes at room temperature. The mixture was passed through a filter with a pore size of 200 nm, and then a phosphate buffer solution of pH 7.4 was added thereto to dilute the mixture to have 1 mg/ml of paclitaxel. The mixture was allowed to stand at 37° C. and the concentration of paclitaxel at different time intervals was measured by HPLC. The results are shown in Table 10.

TABLE 9

| M.W. of | Drug concentration (mg/ml) | | | | | | | | |
|---|---|---|---|---|---|---|---|---|---|
| D,L-PLA-COONa | 0 d | 1 d | 2 d | 3 d | 5 d | 7 d | 10 d | 12 d | 14 d |
| 646 | 1.00 | 0.39 | 0.23 | 0.20 | 0.17 | 0.17 | 0.16 | 0.16 | 0.15 |
| 1,145 | 1.00 | 0.74 | 0.58 | 0.47 | 0.33 | 0.32 | 0.28 | 0.25 | 0.23 |
| 1,500 | 1.00 | 0.98 | 0.91 | 0.80 | 0.54 | 0.51 | 0.46 | 0.36 | 0.36 |
| 2,300 | 1.00 | 1.00 | 0.99 | 0.98 | 0.80 | 0.75 | 0.68 | 0.64 | 0.62 |

TABLE 10

| D,L-PLA-COONa/mPEG-PLA | Drug concentration (mg/ml) | | | | | | | | |
|---|---|---|---|---|---|---|---|---|---|
| (eq. ratio: x/2) | 0 d | 1 d | 2 d | 3 d | 5 d | 7 d | 10 d | 12 d | 14 d |
| 2/2 | 1.00 | 0.25 | 0.20 | 0.14 | 0.12 | 0.10 | 0.08 | 0.08 | 0.07 |
| 4/2 | 1.00 | 0.41 | 0.27 | 0.22 | 0.17 | 0.14 | 0.12 | 0.11 | 0.08 |
| 6/2 | 1.00 | 1.00 | 0.96 | 0.90 | 0.78 | 0.71 | 0.64 | 0.64 | 0.59 |
| 8/2 | 1.00 | 1.00 | 1.00 | 1.00 | 0.98 | 0.95 | 0.90 | 0.85 | 0.80 |
| 10/2 | 1.00 | 1.00 | 1.00 | 0.97 | 0.95 | 0.93 | 0.87 | 0.78 | 0.67 |
| 12/2 | 1.00 | 0.98 | 0.96 | 0.95 | 0.95 | 0.91 | 0.89 | 0.78 | 0.61 |

As shown in Table 10, as the number of equivalents of D,L-PLA-COONa increased, the stability of the polymeric micelles was increased, and was remarkably increased at an equivalent ratio of 6/2 or more. Particularly, the drug concentration after 14 days was a maximum of 0.80 mg/ml, at an equivalent ratio of 8/2.

Experimental Example 6

Blood Retention Test of the $Ca^{2+}$-fixed Paclitaxel-containing Polymeric Micelles To test the bloodstream retention time of $Ca^{2+}$-fixed paclitaxel-containing polymeric micelles, the polymeric micelle compositions were prepared as follows.

(Composition 1) Polymeric Micelles Containing Paclitaxel, a Block Copolymer, Polylactic Acid, and a Metal Ion.

Paclitaxel, mPEG-PLA (Mn: 2,000-1,776), and D,L-PLA-COONa (Mn: 1,145) were admixed at an equivalent ratio of 1:5:20, and then the mixture was dissolved in 5 ml of anhydrous ethanol to prepare a clear solution. Ethanol was removed therefrom using vacuum evaporator to prepare a paclitaxel-containing polymeric composition. Distilled water(4 ml) was added thereto and the mixture was stirred for 10 minutes at 60° C. to prepare a polymeric micelle aqueous solution containing paclitaxel. To the above polymeric micelle solution was added a $CaCl_2$ aqueous solution (concentration: 100 mg/ml) of the same number of equivalents as the D,L-PLA-COONa, and the mixture was stirred for 20 minutes at room temperature. The mixture was passed through a filter with a pore size of 200 nm.

(Composition 2) Mixed Polymeric Micelles Containing Paclitaxel, a Block Copolymer, and Polylactic Acid.

Paclitaxel, MPEG-PLA (Mn: 2,000-1,776) and D,L-PLA-COONa (Mn: 1,145) were admixed at an equivalent ratio of 1:5:20 and then the mixture was dissolved in 5 ml of anhydrous ethanol to prepare a clear solution. Ethanol was removed therefrom using vacuum evaporator to prepare a paclitaxel-containing polymeric composition. Distilled water(4 ml) was added thereto and the mixture was stirred for 10 minutes at 60° C. to prepare a polymeric micelle aqueous solution containing paclitaxel. The mixture was passed through a filter with a pore size of 200 nm.

(Composition 3) Polymeric Micelles Containing Paclitaxel and a Block Copolymer

Paclitaxel and mPEG-PLA (Mn: 2,000-1,776) were admixed at an equivalent ratio of 1:5 and then the mixture was dissolved in 5 ml of anhydrous ethanol to prepare a clear solution. Ethanol was removed therefrom using vacuum evaporator to prepare a paclitaxel-containing polymeric composition. Distilled water(5 ml) was added thereto and the mixture was stirred for 10 minutes at 60° C. to prepare a polymeric micelle aqueous solution containing paclitaxel. The mixture was passed through a filter with a pore size of 200 nm.

TABLE 11

| | mPEG-PLA (mg) | D,L-PLA-COONa (mg) | Paclitaxel (mg) | $CaCl_2$ (mg) | Content of paclitaxel (mg/ml) |
|---|---|---|---|---|---|
| Com. 1 | 436.9 | 536.4 | 20.0 | 52.0 | 3.5 |
| Com. 2 | 436.9 | 536.4 | 20.0 | — | 3.6 |
| Com. 3 | 436.9 | — | 20.0 | — | 3.7 |

For the animal experiments, male Sprague-Dawley rats of 230-250 g were cannulated in the vena femoralis and aorta femoralis. Compositions 1, 2 and 3 were injected in the vena femoralis at a dose of 10 mg/kg over 15 seconds. After injection, 0.3 ml of whole blood was taken from the aorta femoralis at 1, 15, 30, 45 minutes, and at 1, 1.5, 2, 3, 4, 5, 6, 8 hours and then, centrifuged to obtain clear supernatant plasma.

Furthermore, to analyze the plasma concentration of drug, 0.1 ml of the plasma was introduced into a covered glass tube and 0.1 ml of an acetonitrile solution containing the internal standard substance was added thereto. 10 ml of ethyl acetate was added to the above solution and the mixture was vigorously stirred for 30 seconds, and then, centrifuged at 2,500 rpm for 10 minutes. The whole ethyl acetate layer was taken and transferred to a test tube, and then, the organic solvent was completely evaporated at 40° C. under nitrogen flow. Thereto was added 0.1 ml of a 40% (v/v) acetonitrile solution, and the mixture was vigorously stirred for 30 seconds, and then, subjected to HPLC. The conditions for HPLC were as follows:

Injection volume: 0.075 ml

Flow rate: 1.0 ml/min

Wavelength: 227 nm

Mobile phase: 24% aqueous acetonitrile solution for 5 minutes, increased to 58% for 16 minutes, increased to 70% for 2 minutes, decreased to 34% for 4 minutes, and maintained for 5 minutes Column: 4.6×50 nm (C18, Vydac, USA).

Analysis results of the plasma concentrations of the drugs are shown in the following Table 12 and FIG. 6.

TABLE 12

| | Plasma concentration of paclitaxel (μg/ml) | | | | | | | | | | | |
|---|---|---|---|---|---|---|---|---|---|---|---|---|
| | 1 m | 15 m | 30 m | 45 m | 1 h | 1.5 h | 2 h | 3 h | 4 h | 5 h | 6 h | 8 h |
| Com. 1 | 82.6 | 17.8 | 10.1 | 6.5 | 5.4 | 2.8 | 2.1 | 1.2 | 0.70 | 0.46 | 0.32 | 0.18 |
| Com. 2 | 31.8 | 4.1 | 3.0 | 2.2 | 1.7 | 1.2 | 0.71 | 0.33 | 0.23 | 0.13 | 0.08 | 0.04 |
| Com. 3 | 30.4 | 2.4 | 1.6 | 1.1 | 0.90 | 0.66 | 0.39 | 0.17 | 0.09 | 0.07 | 0.03 | 0.02 |

Figure 6:
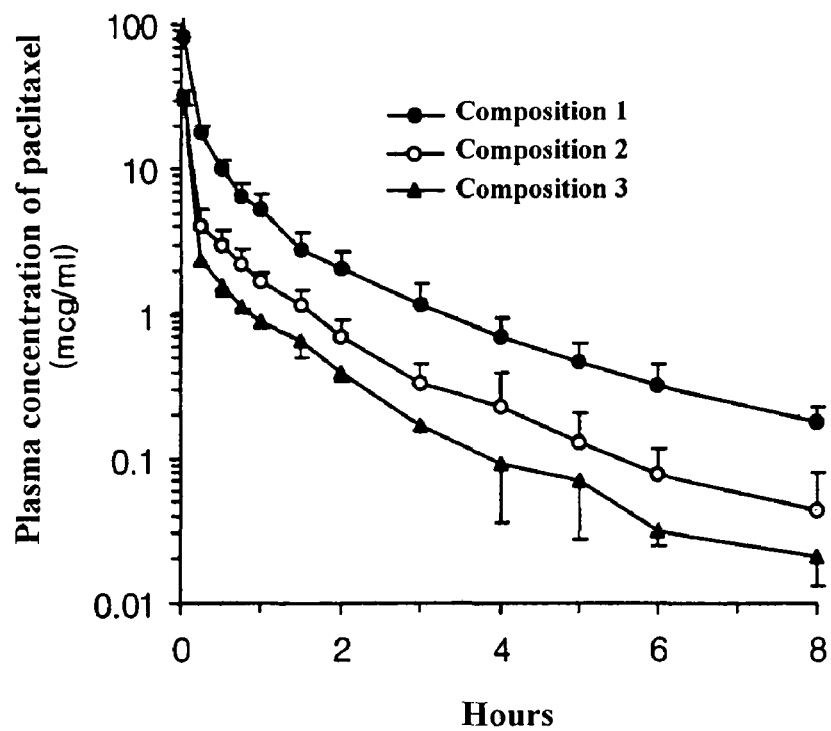
FIG. 6 is a graph showing the plasma drug concentration of a drug-containing $Ca^{2+}$-fixed polymeric micelle at various time intervals after administration.

As shown in Table 12 and FIG. 6, Composition 2 containing D,L-PLA-COONa, had a longer bloodstream retention time than Composition 3 which contained mPEG-PLA block copolymer only, and Composition 1 containing $Ca^{2+}$ had a longer retention time than Composition 2. Therefore, the above results demonstrate that the drug-containing polymeric micelles according to the present invention had a prolonged bloodstream retention time of the drug, and particularly, the metal ion-fixed polymeric micelles had a much prolonged bloodstream retention time of the drug.

Experimental Example 7

Bloodstream Retention Time of $Ca^{2+}$-fixed Paclitaxel-containing Polymeric Micelles To compare the bloodstream retention time of the $Ca^{2+}$-fixed paclitaxel-containing polymeric micelles with that of formulations containing other carriers, the compositions were prepared as follows.

(Composition 4) Polymeric Micelles Containing Paclitaxel, a Block Copolymer, Polylactic Acid, and a Metal Ion.

Paclitaxel, mPEG-PLA (Mn: 2,000-1,776) and D,L-PLMA-COONa (Mn: 1,198) were admixed in a weight ratio of 49.5:49.5:1 and then the mixture was dissolved in 5 ml of anhydrous ethanol to prepare a clear solution. Ethanol was removed therefrom using vacuum evaporator to prepare a paclitaxel-containing polymeric composition. Distilled water(4 ml) was added thereto and the mixture was stirred for 10 minutes at 60° C. to prepare a polymeric micelle aqueous solution containing paclitaxel. To the above polymeric micelle solution was added a $CaCl_2$ aqueous solution (concentration: 100 mg/ml) of the same number of equivalents as the D,L-PLMA-COONa, and the mixture was stirred for 20 minutes at room temperature. The mixture was passed through a filter with a pore size of 200 nm.

(Composition 5) Composition Containing Paclitaxel, Cremophor EL, and Anhydrous Ethanol.

Paclitaxel (30 mg) was dissolved in 5 ml of a mixed solution (50:50 v/v) of Cremophor EL and anhydrous ethanol to obtain a clear solution. The solution was passed through a filter having the pore size of 200 nm.

(Composition 6) Composition Containing Paclitaxel, Polysorbate 80 (Tween 80), and Anhydrous Ethanol Paclitaxel (30 mg) was dissolved in 5 ml of a mixed solution (50:50 v/v) of polysorbate 80 and anhydrous ethanol to obtain a clear solution. The solution was passed through a filter having a pore size of 200 nm.

The above composition and the drug content are summarized in Table 13.

TABLE 13

| Com. 4 | mPEG-PLA (mg) | D,L-PLMA-COONa (mg) | Paclitaxel (mg) | $CaCl_2$ (mg) | Content of paclitaxel (mg/ml) |
|---|---|---|---|---|---|
| | 990 | 990 | 20.0 | 100.6 | 1.6 |
| Com. 5 | Cremophor EL (ml) | Anhydrous ethanol (ml) | Paclitaxel (mg) | — | Content of paclitaxel (mg/ml) |
| | 2.5 | 2.5 | 30.0 | — | 1.5 |
| Com. 6 | Tween 80 (ml) | Anhydrous ethanol (ml) | Paclitaxel (mg) | — | Content of paclitaxel (mg/ml) |
| | 2.5 | 2.5 | 30.0 | — | 1.5 |

For the animal experiments, male Sprague-Dawley rats weighting 230-250 g were cannulated in the vena femoralis and aorta femoralis. Compositions 4, 5 and 6 were injected into the vena femoralis at a dose of 5 mg/kg over 15 seconds. After injection, 0.3 ml of whole blood was taken from aorta femoralis at 1, 15, 30 minutes, and at 1, 1.5, 2, 3, 4, 6 hours and then, centrifuged to obtain clear supernatant plasma.

Figure 7:
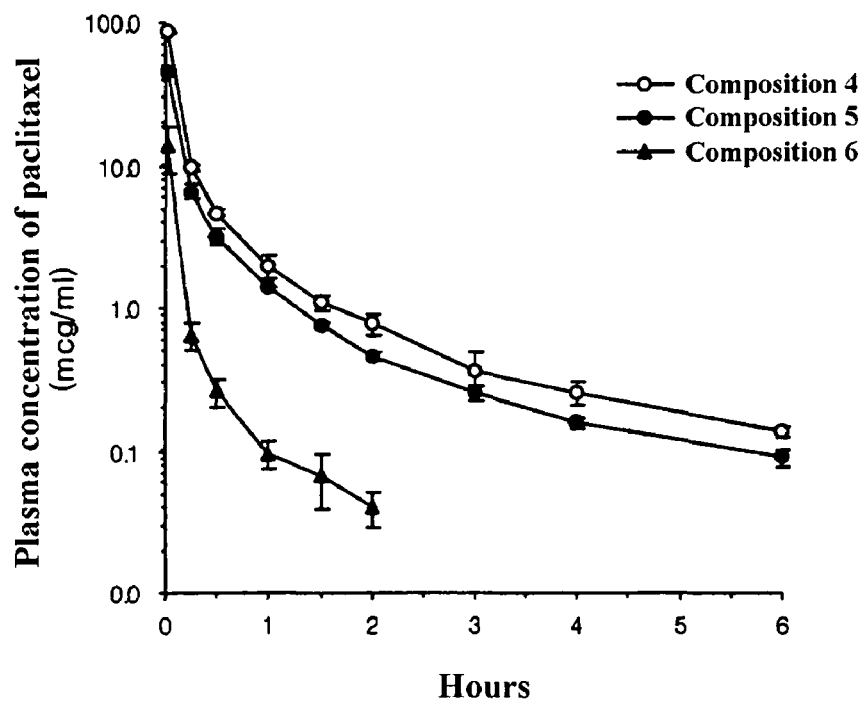
FIG. 7 illustrates the plasma concentration profiles of $Ca^{2+}$-fixed polymeric micelles, Cremophor EL and Tween 80 preparations, respectively.

Furthermore, the plasma drug concentration was analyzed according to the same process as in Experimental Example 6, and the results of the plasma drug concentrations are shown in Table 14 and FIG. 7.

TABLE 14

| | Plasma concentration of paclitaxel (μg/ml) | | | | | | | | |
|---|---|---|---|---|---|---|---|---|---|
| | 1 m | 15 m | 30 m | 1 h | 1.5 h | 2 h | 3 h | 4 h | 6 h |
| Com. 4 | 86.5 | 9.68 | 4.71 | 1.97 | 1.10 | 0.78 | 0.35 | 0.26 | 0.14 |
| Com. 5 | 45.7 | 6.60 | 3.20 | 1.40 | 0.75 | 0.46 | 0.25 | 0.16 | 0.09 |
| Com. 6 | 13.9 | 0.64 | 0.26 | 0.10 | 0.07 | 0.04 | — | — | — |

As shown in Table 14 and FIG. 7, the $Ca^{2+}$-fixed polymeric micelles (Composition 4) had a longer bloodstream retention time than the injections containing other surfactants (Compositions 5 and 6). Since the $Ca^{2+}$-fixed polymeric micelles (Composition 4) of the present invention had a longer bloodstream retention time than the marketed formulation Taxol® (Composition 5), the present invention could increase the drug retention time in the bloodstream over Taxol® by using the biodegradable and biocompatible polymers.

Experimental Example 8

Anticancer Activity of $Ca^{2+}$-fixed Paclitaxel-containing Polymeric Micelles

A 0.1 ml of a cell suspension containing $7\times10^6$ human cancer cells (PPC1, HT29) was subcutaneously injected into the sides of healthy female nude (nu/nu) athymic mice (20 g, 8-week aged, n=6). After the cancers reached a certain size, they were xenografted three times to form xenograft fragments of 3-4 mm. The xenograft fragments were subcutaneously injected to the sides of healthy female nude (nu/nu) athymic mice (20 g, 8-week aged, n=5) with 12 gauge trocar needles. When the volume of cancer reached 100-300 mm³, the drug was administered and this point in time was recorded as day 0. At day 0, the mice were placed to groups of 5, and at days 0, 1, and 2, metal ion-fixed polymeric micelles (Composition 4) and the Cremophor EL formulation (Composition 5) were administered at a dose of 20 mg/kg of paclitaxel through the tail vein, and the volume of the cancer were measured at different time intervals. The volume of cancer was calculated by the formula $(W^2 \times L)/2$ wherein W is a short axis, and L is a long axis.

Figure 8A:
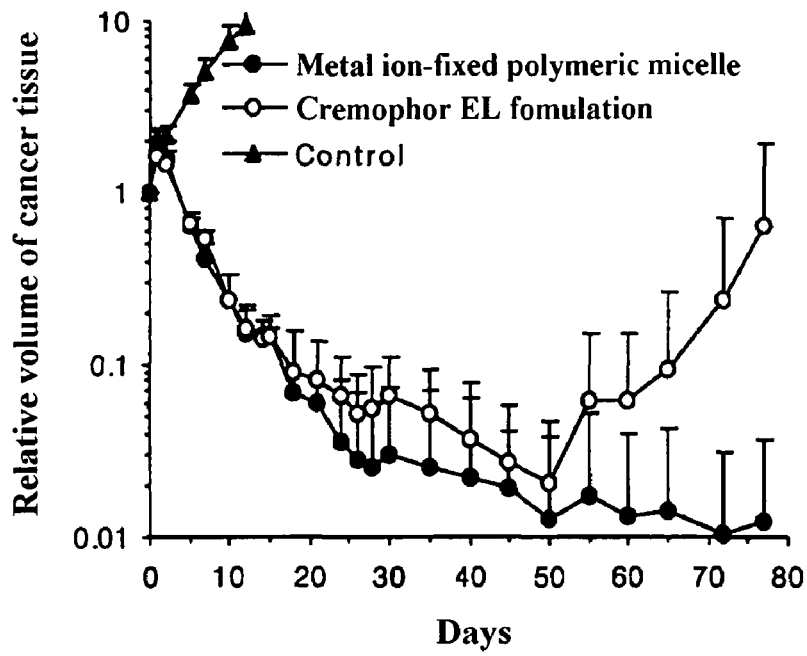
FIG. 8a shows the anticancer effects of drug containing $Ca^{2+}$-fixed polymeric micelles in mice using the human prostatic carcinoma cell line PPC-1.
Figure 8B:
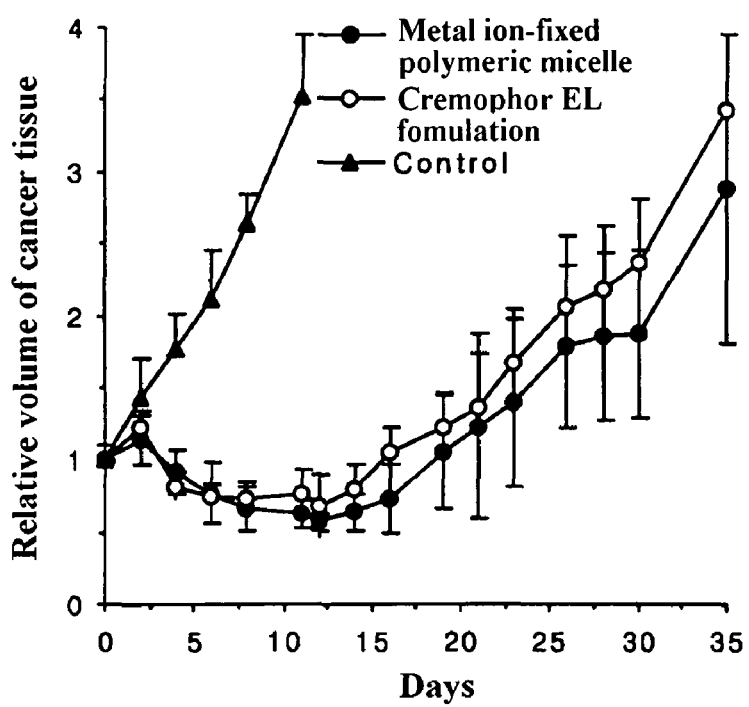
FIG. 8b shows the anticancer effects of drug containing $Ca^{2+}$-fixed polymeric micelles in mice using the human colon cancer cell line HT-29.

As shown in FIGS. 8a and 8b, both the metal ion-fixed polymeric micelle-treated group and the Cremophor EL formulation-treated group showed a considerable inhibition on cancer growth compared with the control group, and particularly, the metal ion-fixed polymeric micelle-treated group showed a higher inhibition rate than the Cremophor EL formulation-treated group.

It is to be understood that the above-described embodiments are only illustrative of the applications of the principles of the present invention. Numerous modifications and alternative embodiments can be derived without departing from the spirit and scope of the present invention and the appended claims are intended to cover such modifications and arrangements. Thus, while the present invention has been shown in the drawings and fully described above with particularity and detail in connection with what is presently deemed to be the most practical and preferred embodiment(s) of the invention, it will be apparent to those of ordinary skill in the art that numerous modifications can be made without departing from the principles and concepts of the invention as set forth in the claims.

We claim:

1. A polymeric micellar composition capable of forming stable micelles in an aqueous solution, said composition comprising an amphiphilic block copolymer of a hydrophilic block and a hydrophobic block, and a polylactic acid derivative, wherein at least one terminal end of said polylactic acid derivative is covalently bound to a carboxylate metal salt, wherein said polyactic acid derivative is a member selected from the group consisting of D,L-polylactic acid, D-polylactic acid, polymandelic acid, a copolymer of D,L-lactic acid and glycolic acid, a copolymer of D,L-lactic acid and mandelic acid, a copolymer of D,L-Lactic acid and caprolactone, and a copolymer of D,L-lactic acid and 1,4-dioxan-2-one, and wherein said polylactic acid derivative has a number average molecular weight of 500 to 2,500 Daltons.

2. The polymeric micellar composition of claim 1, wherein the other terminal end of said polylactic acid derivative is covalently bound to a functional group selected from the group consisting of hydroxyl, acetoxy, benzoyloxy, decanoyloxy and palmitoyloxy groups.

3. The polymeric micellar composition of claim 1, wherein said polylactic acid derivative is represented by the following formula:

RO—CHZ-[A]$_n$-[B]$_m$—COOM  (I)

wherein A is —COO—CHZ—; B is —COO—CHY—, —COO—CH$_2$CH$_2$CH$_2$CH$_2$CH$_2$— or —COO—CH$_2$CH$_2$OCH$_2$—; R is a hydrogen atom, acetyl, benzoyl, decanoyl, palmitoyl, methyl or ethyl group; Z and Y each are a member selected from the group consisting of a hydrogen atom, methyl, or phenyl group; M is H, Na, K, or Li; n is an integer from 1 to 30, and m is an integer from 2 to 20.

4. The polymeric micellar composition of claim 3, wherein said hydrophilic block is a member selected from the group consisting of polyalkylene glycols, polyvinyl pyrrolidone, polyvinyl alcohols and polyacryl amides, and said hydrophobic block is a member selected from the group consisting of polylactides, polyglycolides, polydioxan-2-one, polycaprolactone, polylactic-co-glycolide, polylactic-co-caprolactone, and polylactic-co-dioxan-2-one.

5. The polymeric micellar composition of claim 4, wherein the hydrophilic and hydrophobic blocks have a number average molecular weight within the range of 500 to 50,000 Daltons, respectively.

6. The polymeric micellar composition of claim 3, wherein said hydrophobic block has a hydroxyl terminal group which is substituted with a fatty acid group.

7. The polymeric micellar composition of claim 3, wherein the ratio of the hydrophilic block to the hydrophobic block in the amphiphilic block copolymer is within the range of 2:8 to 8:2.

8. The polymeric micellar composition of claim 3, said composition comprising 5 to 95 wt % of the amphiphilic block copolymer and 5 to 95 wt % of the polylactic acid derivative, based on the total weight of the composition.

9. The polymeric micellar composition of claim 3, wherein said polylactic acid derivative is in a sodium or potassium salt form.

10. The polymeric micellar composition of claim 3, further comprising 0.01 to 0.5 equivalents of a di- or tri-valent metal ion with respect to 1 equivalent of the carboxyl terminal group of the polylactic acid derivative.

11. The polymeric micellar composition of claim 10, wherein the di-or tri-valent metal ion is a member selected from the group consisting of $Ca^{2+}$, $Mg^{2+}$, $Ba^{2+}$, $Cr^{3+}$, $Fe^{3+}$, $Mn^{2+}$, $Ni^{2+}$, $Cu^{2+}$, $Zn^{2+}$, and $Al^{3+}$.

12. A pharmaceutical micellar composition capable of forming stable micelles in an aqueous solution comprising 70 to 99.9 wt % of the polymeric composition of claims 3 and 0.1 to 30 wt % of a poorly water-soluble drug, wherein, when a micelle is formed in aqueous solution the micelle has a hydrophilic outer shell and an inner hydrophobic core, and the drug is physically trapped within the hydrophobic core of the micelle.

13. A nanoparticle-forming polymeric composition, comprising the polymeric micellar composition of claims 3, and 0.5 to 10 equivalents of the di- or tri-valent metal ion with respect to 1 equivalent of the carboxyl terminal group of the polylactic acid derivative.

14. The nanoparticle-forming polymeric composition of claim 13, wherein the di- or tri-valent metal ion is one selected from the group consisting of $Ca^{2+}$, $Mg^{2+}$, $Ba^{2+}$, $Cr^{3+}$, $Fe^{3+}$, $Mn^{2+}$, $Ni^{2+}$ and $Al^{3+}$.

15. A pharmaceutical composition comprising 70 to 99.9 wt % of the nanoparticle-forming polymeric composition of claims 13 and 0.1 to 30 wt% of a poorly water-soluble drug.

16. The polymeric composition of claim 1, wherein said polylactic acid derivative is represented by the following formula:

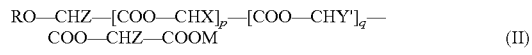

RO—CHZ—[COO—CHX]$_p$—[COO—CHY']$_q$—COO—CHZ—COOM  (II)

wherein X is a methyl group; Y' is hydrogen atom or phenyl group; p and q each are an integer from 0 to 25 provided that p+q is an integer from 5 to 25; R is a hydrogen atom, acetyl, benzoyl, decanoyl, palmitoyl, methyl or ethyl group; Z is a hydrogen atom, methyl, or phenyl group; and M is, Na, K, or Li.

17. The polymeric composition of claim 16, wherein said hydrophilic block is a member selected from the group consisting of polyalkylene glycols, polyvinyl pyrrolidone, polyvinyl alcohols and polyacryl amides, and said hydrophobic block is a member selected from the group consisting of polylactides, polyglycolides, polydioxan-2-one, polycaprolactone, polylactic-co-glycolide, polylactic-co-caprolactone, polylactic-co-dioxan-2-one, and derivatives thereof.

18. The polymeric composition of claim 17, wherein the hydrophilic and hydrophobic blocks have a number average molecular weight within the range of 500 to 50,000 Daltons, respectively.

19. The polymeric composition of claim 16, wherein the hydroxyl terminal group of said hydrophobic block is substituted with a fatty acid group.

20. The polymeric composition of claim 16, wherein the ratio of the hydrophilic block to the hydrophobic block in the amphiphilic block copolymer is within the range of 2:8 to 8:2.

21. The polymeric composition of claim 16 contains 5 to 95 wt % of the amphiphilic block copolymer and 5 to 95 wt % of the polylactic acid derivative, based on the total weight of the composition.

22. The polymeric composition of claim 16, wherein said polylactic acid derivative has a number average molecular weight of 500 to 2,500 Daltons.

23. The polymeric composition of claim 16, wherein said polylactic acid derivative is in a sodium or potassium salt form.

24. The polymeric composition of claim 16, further comprising 0.01 to 0.5 equivalents of a di- or tri-valent metal ion with respect to 1 equivalent of the carboxyl terminal group of the polylactic acid derivative.

25. The polymeric composition of claim 24, wherein the di- or tri-valent metal ion is a member selected from the group consisting of $Ca^{2+}$, $Mg^{2+}$, $Ba^{2+}$, $Cr^{3+}$, $Fe^{3+}$, $Mn^{2+}$, $Ni^{2+}$, $Cu^{2+}$, $Zn^{2+}$, and $Al^{3+}$.

26. A pharmaceutical composition capable of forming stable micelles in an aqueous solution comprising 70 to 99.9 wt % of the polymeric composition of claims 16 and 0.1 to 30 wt % of a poorly water-soluble drug, wherein, when a micelle is formed in aqueous solution the micelle has a hydrophilic outer shell and an inner hydrophobic core, and the drug is physically trapped within the hydrophobic core of the micelle.

27. A nanoparticle-forming polymeric composition, comprising the polymeric composition of claims 16 and 0.5 to 10 equivalents of the di- or tri-valent metal ion with respect to 1 equivalent of the carboxyl terminal group of the polylactic acid derivative.

28. The polymeric composition of claim 27, wherein the di- or tri-valent metal ion is one selected from the group consisting of $Ca^{2+}$, $Mg^{2+}$, $Ba^{2+}$, $Cr^{3+}$, $Fe^{3+}$, $Mn^{2+}$, $Ni^{2+}$, $Cu^{2+}$, $Zn^{2+}$ and $Al^{3+}$.

29. A pharmaceutical composition comprising 70 to 99.9 wt % of the nanoparticle-forming polymeric composition of claims 27 and 0.1 to 30 wt % of a poorly water-soluble drug.

30. The polymeric composition of claim 1, wherein said polylactic acid derivative is represented by the following formula:

RO—PLA-COO—W-M'  (III)

wherein W-M' is

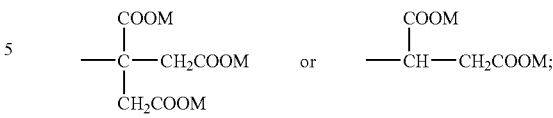

PLA is a member selected from the group consisting of D,L-polylactic acid, D-polylactic acid, polymandelic acid, a copolymer of D,L-lactic acid and glycolic acid, a copolymer of D,L-lactic acid and mandelic acid, a copolymer of D,L-Lactic acid and caprolactone, and a copolymer of D,L-lactic acid and 1,4-dioxan-2-one; R is a hydrogen atom, acetyl, benzoyl, decanoyl, palmitoyl, methyl or ethyl group; and M is, Na, K, or Li.

31. The polymeric composition of claim 30, wherein said hydrophilic block is a member selected from the group consisting of polyalkylene glycols, polyvinyl pyrrolidone, polyvinyl alcohols and polyacryl amides, and said hydrophobic block is a member selected from the group consisting of polylactides, polyglycolides, polydioxan-2-one, polycaprolactone, polylactic-co-glycolide, polylactic-co-caprolactone, polylactic-co-dioxan-2-one, and derivatives thereof.

32. The polymeric composition of claim 31, wherein the hydrophilic and hydrophobic blocks have a number average molecular weight within the range of 500 to 50,000 Daltons, respectively.

33. The polymeric composition of claim 30, wherein said hydrophobic block has a hydroxyl terminal group which is substituted with a fatty acid group.

34. The polymeric composition of claim 30, wherein the ratio of the hydrophilic block to the hydrophobic block in the amphiphilic block copolymer is within the range of 2:8 to 8:2.

35. The polymeric composition of claim 30 contains 5 to 95 wt % of the amphiphilic block copolymer and 5 to 95 wt % of the polylactic acid derivative, based on the total weight of the composition.

36. The polymeric composition of claim 30, wherein said polylactic acid derivative has a number average molecular weight of 500 to 2,500 Daltons.

37. The polymeric composition of claim 30, wherein said polylactic acid derivative is in a sodium or potassium salt form.

38. The polymeric composition of claim 30, further comprising 0.01 to 0.5 equivalents of a di- or tri-valent metal ion with respect to 1 equivalent of the carboxyl terminal group of the polylactic acid derivative.

39. The polymeric composition of claim 38, wherein the di- or tri-valent metal ion is a member selected from the group consisting of $Ca^{2+}$, $Mg^{2+}$, $Ba^{2+}$, $Cr^{3+}$, $Fe^{3+}$, $Mn^{2+Ni2+}$, $Cu^{2+}$, $Zn^{2+}$, and $Al^{3+}$.

40. A pharmaceutical composition capable of forming stable micelles in an aqueous solution comprising 70 to 99.9 wt % of the polymeric composition of claims 30 and 0.1 to 30 wt % of a poorly water-soluble drug, wherein, when a micelle is formed in aqueous solution the micelle has a hydrophilic outer shell and an inner hydrophobic core, and the drug is physically trapped within the hydrophobic core of the micelle.

41. A nanoparticle-forming polymeric composition, comprising the polymeric composition of claims 30, and 0.5 to 10 equivalents of the di- or tri-valent metal ion with respect to 1 equivalent of the carboxyl terminal group of the polylactic acid derivative.

42. The polmeric composition of claim 41, wherein the di- or tri-valent metal ion is one selected from the group consisting of $Ca^{2+}$, $Mg^{2+}$, $Ba^{2+}$, $Cr^{3+}$, $Fe^{3+}$, $Mn^{2+}$, $Ni^{2+}$, $Cu^{2+}$, $Zn^{2+}$ and $Al^{3+}$.

43. A pharmaceutical composition comprising 70 to 99.9 wt % of the nanoparticle-forming polymeric composition of claims 41 and 0.1 to 30 wt % of a poorly water-soluble drug.

44. The polymeric composition of claim 1, wherein said polylactic acid derivative is represented by the following formula:

wherein S is

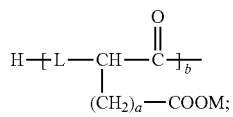

L is $-NR_1-$ or $-O-$; $R_1$ is a hydrogen atom or $C_{1-10}$ alkyl; Q is $CH_3$, $CH_2CH_3$, $CH_2CH_2CH_3$, $CH_2CH_2CH_2CH_3$, or $CH_2C_6H_5$; a is an integer from 0 to 4; b is an integer from 1 to 10; R is a hydrogen atom, acetyl, benzoyl, decanoyl, palmitoyl, methyl or ethyl group; M is, Na, K, or Li and PLA is a member selected from the group consisting of D,L-polylactic acid, D-polylactic acid, polymandelic acid, a copolymer of D,L-lactic acid and glycolic acid, a copolymer of D,L-lactic acid and mandelic acid, a copolymer of D,L-Lactic acid and caprolactone, and a copolymer of D,L-lactic acid and 1,4-dioxan-2-one.

45. The polymeric composition of claim 44, wherein said hydrophilic block is a member selected from the group consisting of polyalkylene glycols, polyvinyl pyrrolidone, polyvinyl alcohols and polyacryl amides, and said hydrophobic block is a member selected from the group consisting of polylactides, polyglycolides, polydioxan-2-one, polycaprolactone, polylactic-co-glycolide, polylactic-co-caprolactone, polylactic-co-dioxan-2-one, and derivatives thereof.

46. The polymeric composition of claim 44, wherein said hydrophobic block has a hydroxyl terminal group which is substituted with a fatty acid group.

47. The polymeric composition of claim 45, wherein the hydrophilic and hydrophobic blocks have a number average molecular weight within the range of 500 to 50,000 Daltons, respectively.

48. The polymeric composition of claim 44, wherein the ratio of the hydrophilic block to the hydrophobic block in the amphiphilic block copolymer is within the range of 2:8 to 8:2.

49. The polymeric composition of claim 44 contains 5 to 95 wt % of the amphiphilic block copolymer and 5 to 95 wt % of the polylactic acid derivative, based on the total weight of the composition.

50. The polymeric composition of claim 44, wherein said polylactic acid derivative has a number average molecular weight of 500 to 2,500 Daltons.

51. The polymeric composition of claim 44, wherein said polylactic acid derivative is in a sodium or potassium salt form.

52. The polymeric composition of claim 44, further comprising 0.01 to 0.5 equivalents of a di- or tri-valent metal ion with respect to 1 equivalent of the carboxyl terminal group of the polylactic acid derivative.

53. The polymeric composition of claim 52, wherein the di- or tri-valent metal ion is a member selected from the group consisting of $Ca^{2+}$, $Mg^{2+}$, $Ba^{2+}$, $Cr^{3+}$, $Fe^{3+}$, $Mn^{2+}$, $Ni^{2+}$, $Cu^{2+}$, $Zn^{2+}$, and $Al^{3+}$.

54. A pharmaceutical composition capable of forming stable micelles in an aqueous solution comprising 70 to 99.9 wt % of the polymeric composition of claims 44 and 0.1 to 30 wt % of a poorly water-soluble drug, wherein, when a micelle is formed in aqueous solution the micelle has a hydrophilic outer shell and an inner hydrophobic core, and the drug is physically trapped within the hydrophobic core of the micelle.

55. A nanoparticle-forming polymeric composition, comprising a polymeric composition of claims 44 and 0.5 to 10 equivalents of the di- or tri-valent metal ion with respect to 1 equivalent of the carboxyl terminal group of the polylactic acid derivative.

56. The polymeric composition of claim 55, wherein the di- or tri-valent metal ion is one selected from the group consisting of $Ca^{2+}$, $Mg^{2+}$, $Ba^{2+}$, $Cr^{3+}$, $Fe^{3+}$, $Mn^{2+}$, $Ni^{2+}$, $Cu^{2+}$, $Zn^{2+}$, and $Al^{3+}$.

57. A pharmaceutical composition comprising 70 to 99.9 wt % of the nanoparticle-forming polymeric composition of claims 55 and 0.1 to 30 wt % of a poorly water-soluble drug.

58. The polymeric micellar composition of claim 1, wherein said hydrophilic block is a member selected from the group consisting of polyalkylene glycols, polyvinyl pyrrolidone, polyvinyl alcohols and polyacryl amides, and said hydrophobic block is a member selected from the group consisting of polylactides, polyglycolides, polydioxan-2-one, polycaprolactone, polylactic-co-glycolide, polylactic-co-caprolactone, and polylactic-co-dioxan-2-one.

59. The polymeric micellar composition of claim 58, wherein the hydrophilic and hydrophobic blocks have a number average molecular weight within the range of 500 to 50,000 Daltons, respectively.

60. The polymeric micellar composition of claim 1, wherein said hydrophobic block has a hydroxyl terminal group which is substituted with a fatty acid group.

61. The polymeric micellar composition of claim 1, wherein the ratio of the hydrophilic block to the hydrophobic block in the amphiphilic block copolymer is within the range of 2:8 to 8:2.

62. The polymeric micellar composition of claim 1, said composition comprising 5 to 95 wt % of the amphiphilic block copolymer and 5 to 95 wt % of the polylactic acid derivative, based on the total weight of the composition.

63. The polymeric micellar composition of claim 1, wherein said polylactic acid derivative is in a sodium or potassium salt form.

64. The polymeric micellar composition of claim 1, further comprising 0.01 to 0.5 equivalents of a di- or tri-valent metal ion with respect to 1 equivalent of the carboxyl terminal group of the polylactic acid derivative.

65. The polymeric micellar composition of claim 64, wherein the di- or tri-valent metal ion is a member selected from the group consisting of $Ca^{2+}$, $Mg^{2+}$, $Ba^{2+}$, $Cr^{3+}$, $Fe^{3+}$, $Mn^{2+}$, $Ni^{2+}$, $Cu^{2+}$, $Zn^{2+}$ and $Al^{3+}$.

66. A pharmaceutical composition capable of forming stable micelles in an aqueous solution comprising
70 to 9.9 wt % of the polymeric micellar composition of claims 1 and
0.1 to 30 wt % of a poorly water-soluble drug,
wherein, when a micelle is formed in aqueous solution the micelle has a hydrophilic outer shell and an inner hydrophobic core, and the drug is physically trapped within the hydrophobic core of the micelle.

67. A nanoparticle-forming polymeric composition, comprising the polymeric micellar composition of claims 1, and 0.5 to 10 equivalents of the di- or tri-valent metal ion with respect to 1 equivalent of the carboxyl terminal group of the polylactic acid derivative.

68. The nanoparticle-forming polymeric composition of claim 67, wherein the di- or tri-valent metal ion is one selected from the group consisting of $Ca^{2+}$, $Mg^{2+}$, $Ba^{2+}$, $Cr^{3+}$, $Fe^{3+}$, $Mn^{2+}$, $Ni^{2+}$, $Cu^{2+}$, $Zn^{2+}$ and $Al^{3+}$.

69. A pharmaceutical composition comprising 70 to 99.9 wt % of the nanoparticle-forming polymeric composition of claims 68 and 0.1 to 30 wt % of a poorly water-soluble drug.

70. A process for preparing a pharmaceutical composition capable of forming stable micelles in an aqueous solution comprising the steps of
dissolving 70 to 99.9 wt % of the polymeric micellar composition of claims 1 and 0.1 to 30 wt % of a poorly water-soluble drug in an organic solvent,
evaporating said organic solvent, and
then adding an aqueous solution to form a micelle solution,
wherein the micelle has a hydrophilic outer shell and an inner hydrophobic core, and the drug is physically trapped within the hydrophobic core of the micelle with the drug being physically trapped within the hydrophobic core of the micelle.

71. The process of claim 70, further comprising the step of adding a di- or tri-valent metal ion to the poorly water-soluble drug-containing polymeric micelles to fix the carboxyl terminal group of the polylactic acid derivative.

72. The process of claim 71, wherein the di- or tri-valent metal ion is one selected from the group consisting of $Ca^{2+}$, $Mg^{2+}$, $Ba^{2+}$, $Cr^{3+}$, $Fe^{3+}$, $Mn^{2+}$, $Ni^{2+}$, $Cu^{2+}$, $Zn^{2+}$ and $Al^{3+}$.

73. The process of claim 70, wherein the organic solvent is one or more selected from the group consisting of acetone, ethanol, methanol, ethyl acetate, acetonitrile, methylene chloride, chloroform, acetic acid, and dioxane.

* * * * *